(12) United States Patent
Allen et al.

(10) Patent No.: US 8,232,397 B2
(45) Date of Patent: Jul. 31, 2012

(54) PROCESSES FOR THE PRODUCTION OF BUPRENORPHINE WITH REDUCED IMPURITY FORMATION

(75) Inventors: Brenda E. Allen, Fieldon, IL (US); Esa T. Jarvi, Ballwin, MO (US); Dennis J. Kalota, Fenton, MO (US); James R. Meyer, St. Louis, MO (US); Keith G. Tomazi, Florissant, MO (US); Anthony Mannino, Maryland Heights, MO (US); Brian Orr, O'fallon, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 459 days.

(21) Appl. No.: 12/586,855

(22) Filed: Sep. 29, 2009

(65) Prior Publication Data

US 2010/0087647 A1    Apr. 8, 2010

Related U.S. Application Data

(60) Provisional application No. 61/194,777, filed on Sep. 30, 2008.

(51) Int. Cl.
C07D 489/12    (2006.01)
C07D 489/02    (2006.01)

(52) U.S. Cl. .......................................... 546/39; 546/44

(58) Field of Classification Search .................... 546/39, 546/44
See application file for complete search history.

(56) References Cited

U.S. PATENT DOCUMENTS

| | | | |
|---|---|---|---|
| 3,433,791 | A | 3/1969 | Bentley et al. |
| 3,763,167 | A | 10/1973 | Hydro |
| 3,905,981 | A | 9/1975 | Olofson et al. |
| 4,613,668 | A | 9/1986 | Rice |
| 5,633,259 | A | 5/1997 | Qin et al. |
| 5,849,915 | A | 12/1998 | Kim et al. |
| 6,291,675 | B1 | 9/2001 | Coop et al. |
| 6,395,900 | B1 | 5/2002 | Coop et al. |
| 2002/0045755 | A1 | 4/2002 | Coop et al. |
| 2003/0194420 | A1 | 10/2003 | Holl et al. |
| 2004/0077863 | A1 | 4/2004 | Scammells et al. |
| 2005/0164358 | A1 | 7/2005 | Carnell et al. |
| 2008/0045715 | A1 | 2/2008 | Mitchell et al. |
| 2008/0312441 | A1 | 12/2008 | Mannino et al. |

FOREIGN PATENT DOCUMENTS

| | | |
|---|---|---|
| CN | 1939920 | 4/2007 |
| EP | 1 439 179 | 7/2004 |
| GB | 902659 | 8/1962 |
| HU | 76478 | 9/1997 |
| WO | WO 03/024972 | 3/2003 |

OTHER PUBLICATIONS

Uff et al., Magnetic Resonance in chemistry, 23(6), 1985, XP 002558538.

Bentley et al., "Novel Analgesics and Molecular . . .", Journal of the American Chemical Society, 89(13), 1967, pp. 3267-3273.
Bentley et al., "Novel Analgesics and Molecular Rearrangements in the Morphine-Thebaine Group . . .", Journal of the American Chemical Society, 1967, 89(13), pp. 3281-3292.
Breeden et al., "6-0-Demethylation of the Thevinols . . .", Helvetica Chimica Acta, 1999, 82(11), pp. 1978-1980.
Grundt et al., "Formic Acid Catalyzed Rearrangement of Thevinols . . .", Helv. Chim. Acta, 86(7), 2003, pp. 2287-2298, XP 002560362.
Henderson et al., "Synthesis from Thebaine of 10-oxothebaine . . .", J. Chem. Soc., 1994, (3), pp. 295-297.
Hori et al., "Synthesis of the novel Sulfur-Containing . . .", Chemical and Pharmaceutical bulletin, 1984, 32(3), pp. 1268-1271.
Iwamura et al., "Synthesis of 6,14-ethenomorphines and the Cytostatic Activity of Tumor Cells", Gifu yakka Daigaku Kiyo, 2005, 54, pp. 45-50.
Leonard et al., "Determination of the Relative and Absolute Configuration . . . ", Organic Letters, 4(4), 2002, pp. 4201-4204, XP 002560364.
Leonard et al., "Determination of the Relative and Absolute Configuration . . . ", Organic Letters Supporting Information, 2002, XP 002563404.
Lewis, "Rinc C-Bridged Derivatives of Thebaine and Oripavine", Advances in biochemical Psychopharmacology, 1973, 8, pp. 123-126.
Li et al., "Selective Demethylation Process in Synthesis of Etorphine and Hydrotorphine", Guanxi Daxue Xuebao, Ziran Kexueban, 2004, 29(3), pp. 265-268.
Ma, Sicai et al., "Improved Synthesis of Diprenorphine", Zhongguo Yixao Gongye Zazhi, 1992, 23(40, pp. 157-158.
Marton et al., "Synthesis of N-Substituted 7B-Diprenorphine Derivatives", Synthetic comm.., 25(6), 1995, pp. 829-848.
Maxichen et al., "Synthesis of the Highly Efficient . . . ", Jingxi Huagong, 1996, 13(1), pp. 12-15.
Russell et al., "One-Pot synthesis Aids Scale-Up and Data Collection", Pharmaceutical Technology, Advanstar Communications, Inc. US, no. Nov. 1, 2003, pp. 17, 22, XP 002433225.
Valhari et al., "Formation of 6,14-endo-ethenotetrahydrothebaine . . . ", Science International, 1992, 4(1), pp. 53-58.
Wan et al., "Synthesis of an Opiate Receptor . . . ", Shangha Dixi Yixueyuan Xuebao, 1985, 12(1), pp. 25-30.
Wang et al., "Synthesis of 3-H-thienorphine", Zhongguo Xinyao Zazhi, 2004, 13(11), pp. 1012-1015.
Woudenberg et al., "Chemistry of Opium Alkaloids . . .", Recuell des Travaux Chimiques des Pays-Bas, 1990, 109(5), pp. 353-357.
Bentley et al., "Novel Analgesics and Molecular Rearrangements in the Morphine-Thebaine Group. II. Alcohols Derived from 6,14-endo-Etheno-and 6,14-endo-Ethanotetrahydrothebaine", Journal of the American Chemical Society, 89(13), Jun. 21, 1967, pp. 3273-3280.
Bentley et al., "New Potent Analgesics in the Morphine Series", Proc. Chem. Soc., Jul. 1963, p. 220.
Bentley et al., "Novel Analegesics and Molecular Rearrangements in the Morphine-Thebaine Group. Part X. Further Acid-catalysed Rearrangements of Alcohols in the 6,14-endo-Ethenotetrahydrothebaine Series", Journal of the American Chemical Society, (C), 1969, pp. 2229-2232.
Bentley et al., "Novel Analegesics and Molecular Rearrangements in the Morphine-Thebaine Group. Part VI Base-Catalyzed Rearrangments in the 6,14-endo-Ethenotetrahydrothebaine Series", Journal of the American Chemical Society, 89:13, 1967, pp. 3312-3321.

(Continued)

Primary Examiner — Charanjit Aulakh

(57) ABSTRACT

The present invention provides process for the production of opiate alkaloids. In particular, the present invention provides processes for the production of buprenorphine or a derivative of buprenorphine that minimizes the formation of impurities.

20 Claims, 2 Drawing Sheets

OTHER PUBLICATIONS

Cone et al., "Stability of the 6,14-*endo*-Ethanotetrahydrooripavine Analgescis: Acid-Catalyzed Rearrangement of Buprenorphine", Journal of Pharmaceutical Sciences, 73(2), Feb. 1984, pp. 243-246.

Lewis et al., "Novel Analgesics and Molecular Rearrangements in the Morphine-Thebaine Group. Part XXVII. 7-Alkylidene- and 7a-Vinyl-6,14-*endo*-etheno-6,7,8,14-tetrahydrothebaines", J. Chem. Soc., (C), 1971, pp. 881-884.

Marton et al., "Studies on the Synthesis of β-Thevinone Derivatives", Tetrahedron, 54, 1998, pp. 9143-9152.

Marton et al., "Herstellung von 6,14-Ethenomorphinan-Derivaten", Monatshefte für Chemie, 125, 1994, pp. 1229-1239.

Letter from CW Woodworth, Lederle Laboratories, American Cyanamid, Apr. 13, 1976 to George B. Vermont, Director, R&D, Mallinckrodt. Procedure for making buprenorphine.

Norwich-Eaton Pharmaceuticals, ~1970's. Procedure for making buprenorphine.

PROCESSES FOR THE PRODUCTION OF BUPRENORPHINE WITH REDUCED IMPURITY FORMATION

CROSS REFERENCE TO RELATED APPLICATIONS

This application claims priority from U.S. Provisional Application No. 61/194,777, filed on Sep. 30, 2008, which is hereby incorporated by reference in its entirety.

FIELD OF THE INVENTION

The present invention generally relates to processes for the synthesis of buprenorphine or derivatives of buprenorphine. In particular, the present invention provides processes for the formation of these opiate compounds that minimizes the formation of impurities.

BACKGROUND OF THE INVENTION

Buprenorphine is a semi-synthetic opiate with partial agonist and antagonist actions. As such, it is a powerful analgesic that is approximately twenty-five to forty times as potent as morphine and is indicated for the treatment of moderate to severe chronic pain or for pre-operative analgesia. Buprenorphine is also used to treat opiate addiction. Accordingly, the demand for buprenorphine is increasing. Processes for synthesizing buprenorphine have been known since the late 1960s; it is traditionally made from either thebaine or oripavine in multiple steps. However, overall yield is typically low and the final product has levels of impurities that exceed the currently prescribed guidelines established by the International Conference on Harmonisation of Technical Requirements for Registration of Pharmaceuticals for Human Use (ICH) and the United States Pharmacopeial Convention (USP). A need, therefore, exists for efficient processes that increase the yield of buprenorphine while minimizing the formation of side products, wherein the final product has a level of purity that meets current ICH and USP standards.

SUMMARY OF THE INVENTION

Briefly, therefore, the present invention provides an improved synthesis route that increases the yield and purity of buprenorphine or a derivative of buprenorphine. Accordingly, one aspect of the invention encompasses a process the preparation of a compound comprising Formula (VII) according to the following reaction scheme:

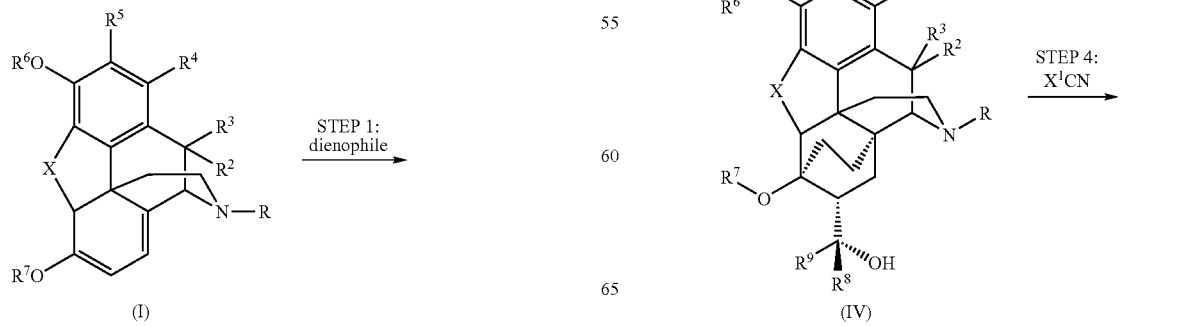

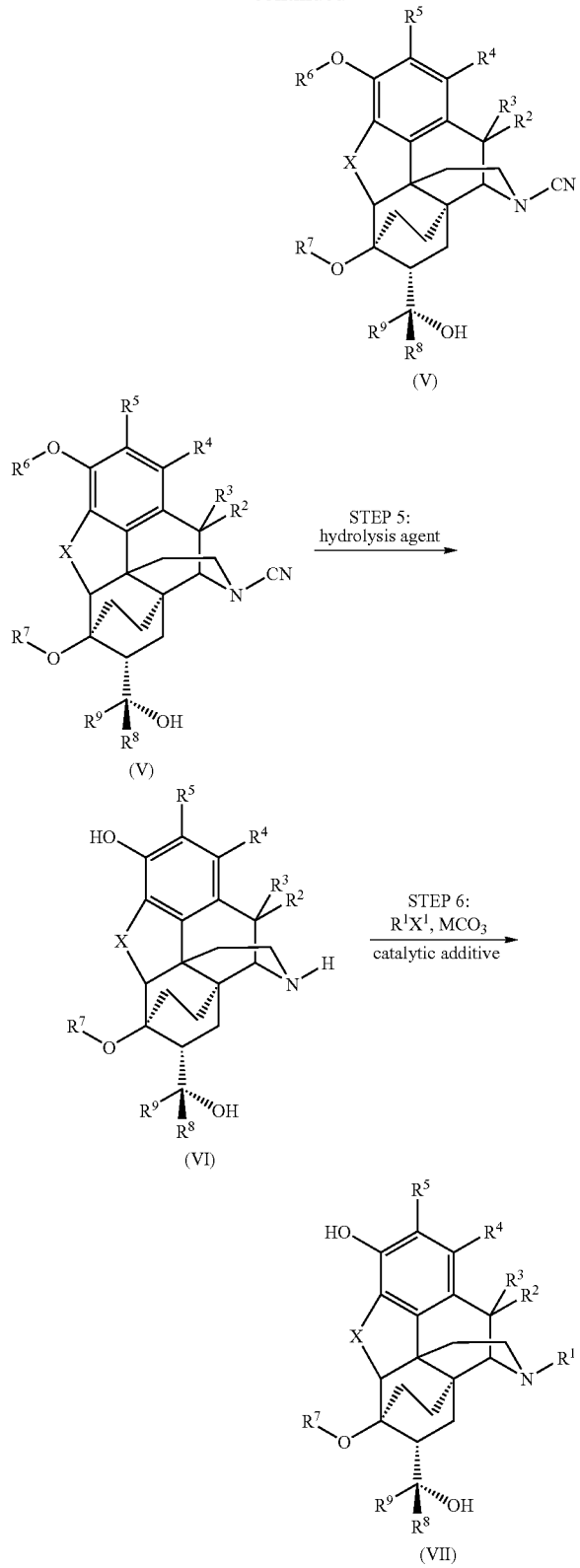

$R^2$ and $R^3$ are independently selected from the group consisting of hydrogen, hydrocarbyl and substituted hydrocarbyl;

$R^4$ and $R^5$ are independently selected from the group consisting of hydrogen, hydrocarbyl, substituted hydrocarbyl, halogen, {—}OH, {—}NH$_2$, {—}SH, {—}SR$^{10}$, and {—}OR$^{10}$;

$R^6$ and $R^7$ are independently selected from the group consisting of hydrogen, a protecting group, hydrocarbyl, and substituted hydrocarbyl;

$R^8$, $R^9$, and $R^{10}$ are independently selected from the group consisting of hydrocarbyl and substituted hydrocarbyl;

M is selected from the group consisting of a metal cation having a charge of $^+1$, and a metal cation group having a charge of $^+2$;

X is a heteroatom; and $X^1$ is a halogen.

The process comprises six steps. The first step comprises contacting a compound comprising Formula (I) with a dienophile to form a compound comprising Formula (II). The second step comprises hydrogenating the compound comprising Formula (II) to form a compound comprising Formula (III). The third step of the process comprises contacting the compound comprising Formula (III) with $R^9MgX^1$ to form the compound comprising Formula (IV). The fourth step comprises contacting the compound comprising Formula (IV) with $X^1CN$ to form the compound comprising Formula (V). The fifth step comprises contacting the compound comprising Formula (V) with a hydrolysis agent to form the compound comprising Formula (VI). The sixth step comprises contacting the compound comprising Formula (VI) with $MCO_3$, a catalytic additive, and $R^1X^1$, the amount of alkenyl impurity in $R^1X^1$ being less than 0.15% by weight, and heating the reaction mixture to a temperature of less than 60° C. to form the compound comprising Formula (VII).

Additional aspects and iterations of the invention are described in more detail below.

DETAILED DESCRIPTION

Figure 1:
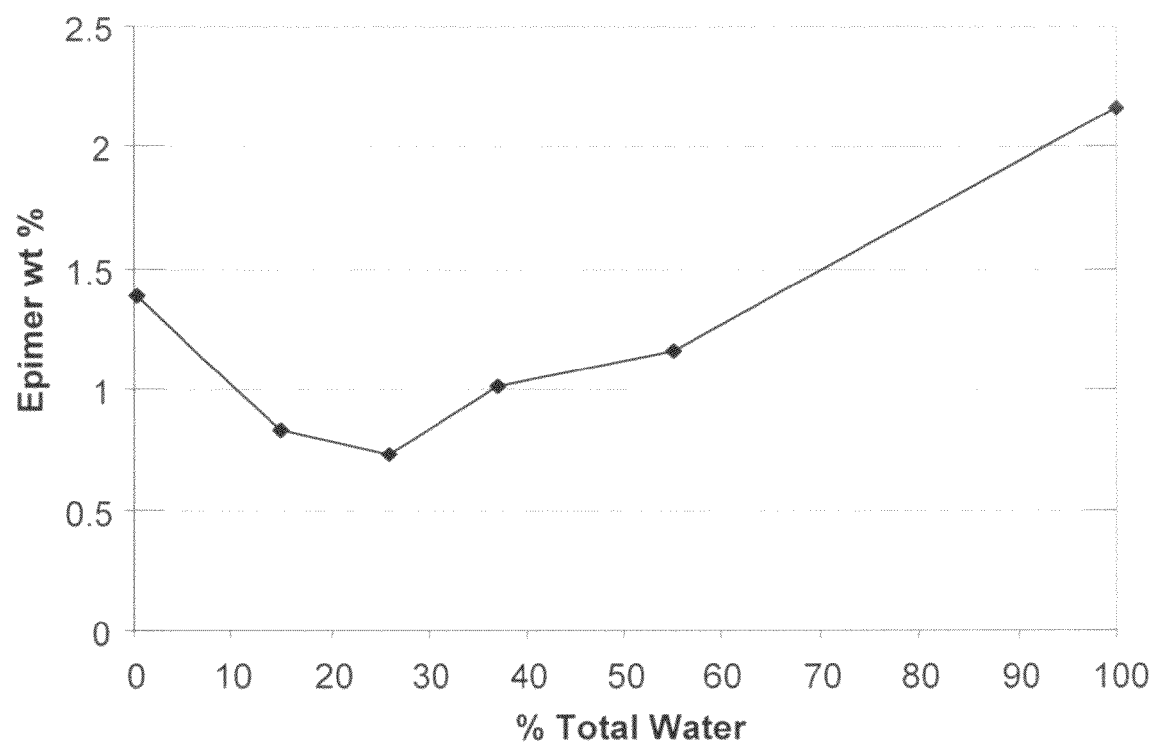
FIG. 1 depicts a graph that illustrates the correlation between the amount of 7-β epimer formed as the percentage (v/v) of water increases during the reaction of step 1 in which thebaine (compound (Ia)) reacts with methyl vinyl ketone to produce 6,14-endo-etheno-7α-acetyltetrahydrothebaine (compound (IIa)). The graph depicts use of six different amounts of water, namely 0% (v/v), 15% (v/v), 26% (v/v), 37% (v/v), 55% (v/v), and 100% (v/v). As shown in the graph, 0% (v/v) of water results in the formation of 1.401% by weight of the 7-β epimer, 15% (v/v) of water results in the formation of 0.828% by weight of the 7-β epimer, 26% (v/v) of water results in the formation of 0.724% by weight of the 7-β epimer, 37% (v/v) of water results in the formation of 1.010% by weight of the 7-β epimer, 55% (v/v) of water results in the formation of 1.155% by weight of the 7-β epimer, and 100% (v/v) of water results in the formation of 2.160% by weight of the 7-β epimer. The reactions were conducted in accordance with the procedures described in Example 1.

The present invention provides an efficient synthetic route for producing buprenorphine or derivatives of buprenorphine wherein:

R is an alkyl or substituted alkyl;

$R^1$ is selected from the group consisting of an alkyl, a substituted alkyl, and a cycloalkyl;

in high yield and high purity. In particular, processes have been discovered that efficiently convert a substrate to the desired product and reduce or eliminate side reactions that give rise to impurities in the final product. Reduction in the levels of impurities ultimately increases the overall yield of buprenorphine or a derivative of buprenorphine. In particular, the overall yield of buprenorphine or a derivative of buprenorphine is increased to greater than about 10% and the level of any related impurity is less than or equal to about 0.15% by weight.

The synthetic route generally encompasses a six-step process for the production of buprenorphine or derivatives of buprenorphine (e.g., a compound comprising Formula VII) from thebaine, derivatives of thebaine, oripavine and/or derivatives of oripavine (e.g., a compound comprising Formula (I)). For purposes of illustration, Reaction Scheme 1 depicts the production of the compound comprising Formula (VII) from the compound comprising Formula (I) in accordance with one aspect of the present invention:

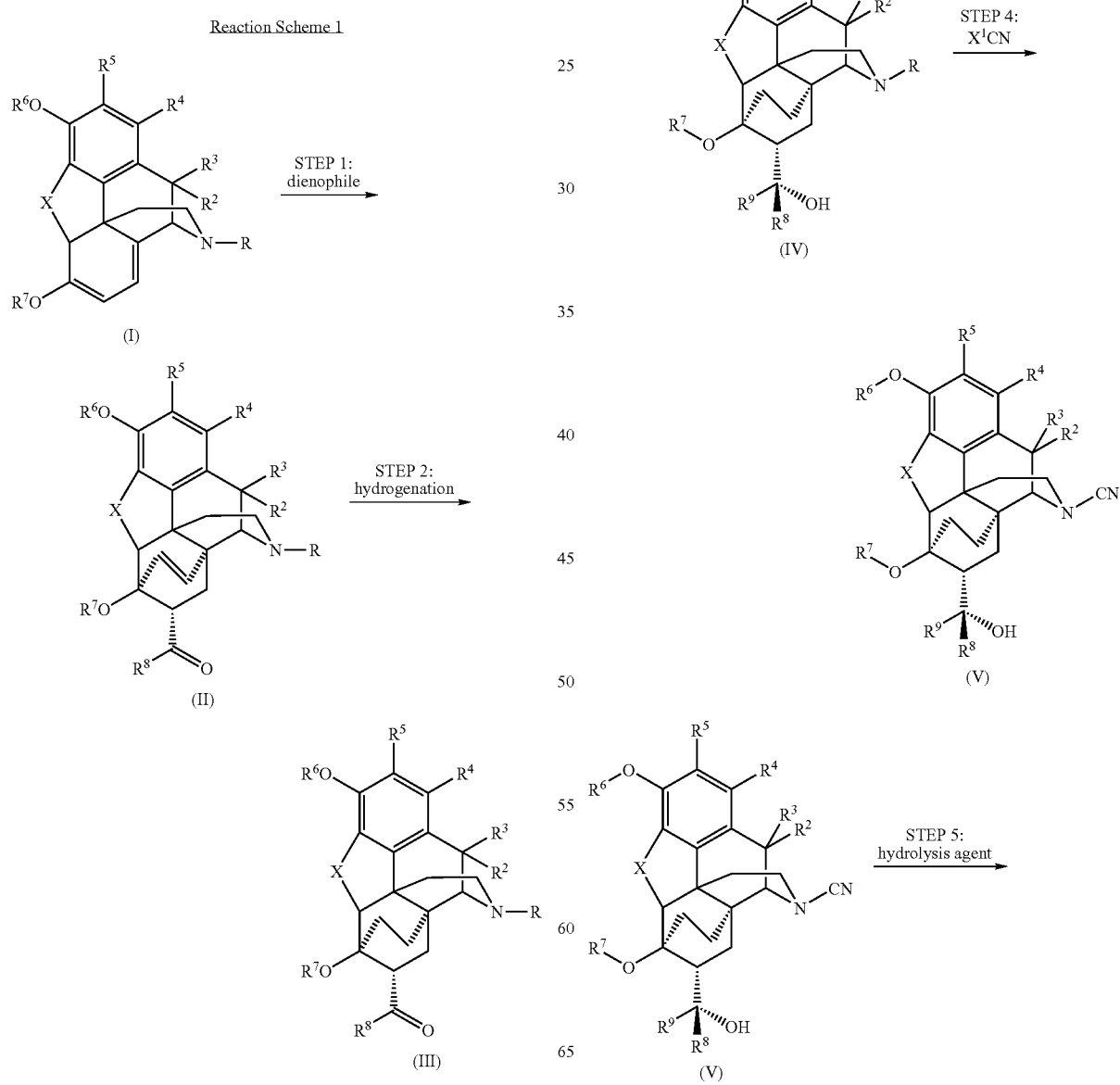

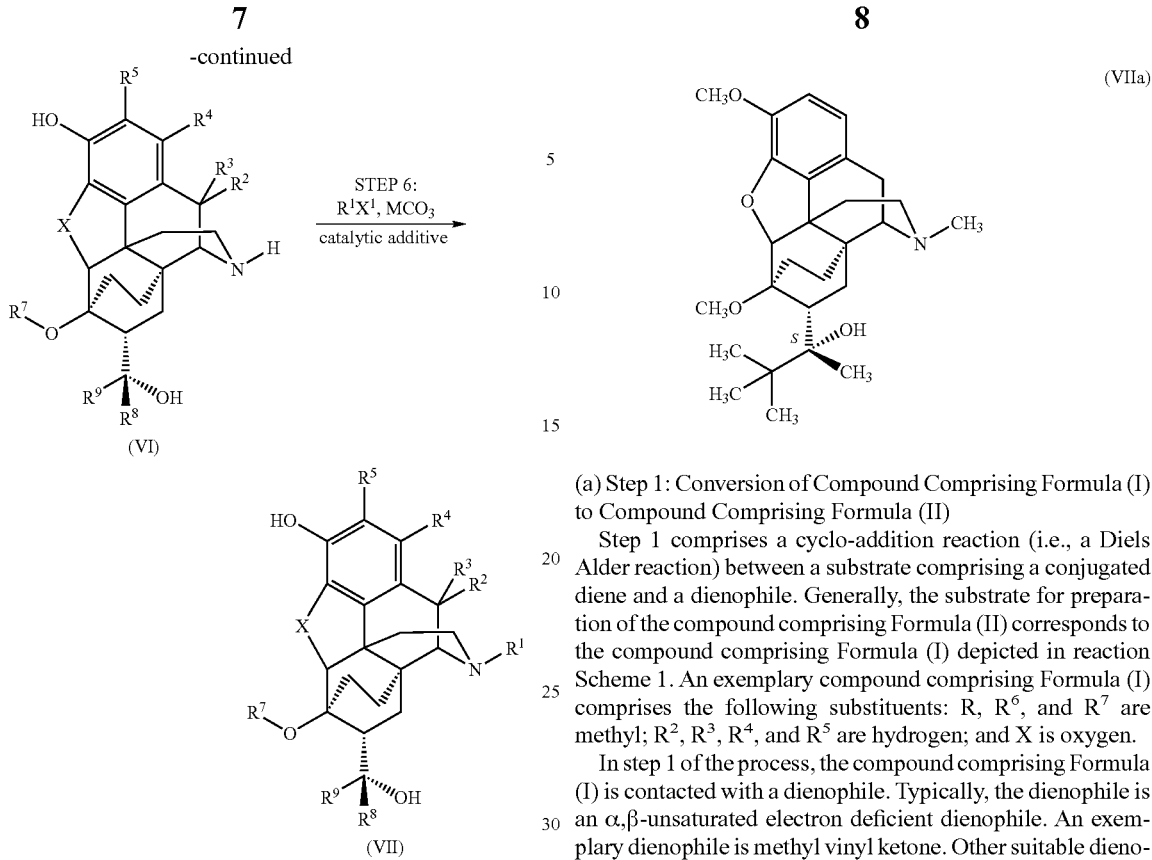

wherein:

R is an alkyl or substituted alkyl;

$R^1$ is selected from the group consisting of an alkyl, a substituted alkyl, and a cycloalkyl;

$R^2$ and $R^3$ are independently selected from the group consisting of hydrogen, hydrocarbyl and substituted hydrocarbyl;

$R^4$ and $R^5$ are independently selected from the group consisting of hydrogen, hydrocarbyl, substituted hydrocarbyl, halogen, {—}OH, {—}$NH_2$, {—}SH, {—}$SR^{10}$, and {—}$OR^{10}$;

$R^6$ and $R^7$ are independently selected from the group consisting of hydrogen, a protecting group, hydrocarbyl, and substituted hydrocarbyl;

$R^8$, $R^9$, and $R^{10}$ are independently selected from the group consisting of hydrocarbyl and substituted hydrocarbyl;

M is selected from the group consisting of a metal cation having a charge of $^+1$, and a metal cation group having a charge of $^+2$;

X is a heteroatom; and $X^1$ is a halogen.

In one embodiment, R, $R^6$, $R^7$, $R^8$ and $R^9$ are alkyl or substituted alkyl, $R^1$ is cycloalkyl or substituted cycloalkyl, and X is oxygen. In an iteration of this embodiment, $R^2$, $R^3$, $R^4$, and $R^5$ are hydrogen. In another embodiment, $R^2$, $R^3$, $R^4$, and $R^5$ are hydrogen. In an iteration of this embodiment, X is oxygen. In a further embodiment, R, $R^6$, $R^7$ and $R^8$ are methyl and $R^1$ is methylcyclopropyl. In an iteration of this embodiment, X is oxygen. In an alternate embodiment, $R^9$ is tertiary butyl. In yet another alternate embodiment, $R^9$ is an alkyl or substituted alkyl and $X^1$ is chloride or bromide.

In an exemplary embodiment, the compound comprising Formula (VII) is the compound comprising Formula (VIIa):

(a) Step 1: Conversion of Compound Comprising Formula (I) to Compound Comprising Formula (II)

Step 1 comprises a cyclo-addition reaction (i.e., a Diels Alder reaction) between a substrate comprising a conjugated diene and a dienophile. Generally, the substrate for preparation of the compound comprising Formula (II) corresponds to the compound comprising Formula (I) depicted in reaction Scheme 1. An exemplary compound comprising Formula (I) comprises the following substituents: R, $R^6$, and $R^7$ are methyl; $R^2$, $R^3$, $R^4$, and $R^5$ are hydrogen; and X is oxygen.

In step 1 of the process, the compound comprising Formula (I) is contacted with a dienophile. Typically, the dienophile is an α,β-unsaturated electron deficient dienophile. An exemplary dienophile is methyl vinyl ketone. Other suitable dienophiles include but are not limited to maleic anhydride, methyl acrylate, diethyl fumarate, benzoquinone, acetylene, 4-phenyl-1,2,4-triazolin-3,4-dione, and 2-methyl-propenal. The molar ratio of the compound comprising Formula (I) to the dienophile can and will vary. Typically, the molar ratio of the compound comprising Formula (I) to the dienophile may range from about 1:1.5 to about 1:5.5. In a preferred embodiment, the molar ratio of the compound comprising Formula (I) to the dienophile may range from about 1:1.75 to 1:3. In certain preferred embodiments, the molar ratio of the compound comprising Formula (I) to the dienophile may be about 1:1.75, 1:2.0, 1:2.25, 1:2.5, 1:2.75, or 1:3.0.

Contact between the compound comprising Formula (I) and the dienophile occurs in a solvent comprising water. As shown in Example 1 and FIG. 1, the inclusion of water within an optimized range minimizes the formation of impurities, and in particular, the β-epimer of the compound comprising Formula (II). As such, the solvent may comprise at least 5%, 10%, 15%, 20%, 25%, 30%, 35%, 40%, 45%, 50%, 55%, 60%, 65%, 70%, 75%, 80%, 85%, 90%, 95%, or 100% water. While it is envisioned that the solvent could comprise 100% water, typically at least one additional solvent is included. Suitable solvents to combine with water preferably include water miscible solvents. Suitable examples of water miscible solvents include but are not limited to alcohols, glycols, dimethyoxyethane (glyme), THF, DMF, NMP, and pyridine. In an exemplary embodiment, the solvent will comprise water and at least one alcohol. The arrangement of carbon atoms comprising the alcohol may be linear, branched or combinations thereof. Exemplary alcohols include methanol, ethanol, isopropanol, n-propanol, isobutanol, t-butanol, n-butanol, and combinations thereof. In a preferred embodiment, the solvent will comprise from about 10% to about 35% by volume water with the balance being alcohol.

In general, the reaction of step 1 may be conducted at a temperature that ranges from about 50° C. to about 100° C. for a period of time that is sufficient to convert a substantial portion of the compound comprising Formula (I) to the compound comprising Formula (II). In a preferred embodiment, the temperature of the reaction may range from about 75° C. to about 85° C. The reaction is preferably performed under ambient pressure, and preferably in an inert atmosphere (e.g., nitrogen or argon).

Typically, the reaction is allowed to proceed for a sufficient period of time until the reaction is complete, as determined by chromatography (e.g., HPLC). In this context, a "completed reaction" generally means that the reaction mixture contains a significantly diminished amount of a compound comprising Formula (I) and a significantly increased amount of the compound comprising Formula (II) compared to the amounts of each present at the beginning of the reaction. Typically, the amount of the compound comprising Formula (I) remaining in the reaction mixture may be less than about 0.01%.

When the reaction is completed, the reaction mixture is cooled. Typically, as detailed in Example 1, the reaction mixture is cooled from the reaction temperature (i.e., around 80° C.) to about room temperature then to about 5° C. As the reaction mixture is cooled, the compound comprising Formula (II) typically crystallizes out of the reaction mixture. The reaction mixture at this point comprises the solvent, the unreacted compound comprising Formula (I), and the dienophile. Since the product crystallizes out directly after the one-pot reaction, the compound comprising Formula (II) may be easily separated from the reaction mixture without solvent distillation. This beneficially avoids the need to handle the reaction mixture comprising the dienophile in order to isolate the reaction product.

Figure 2:
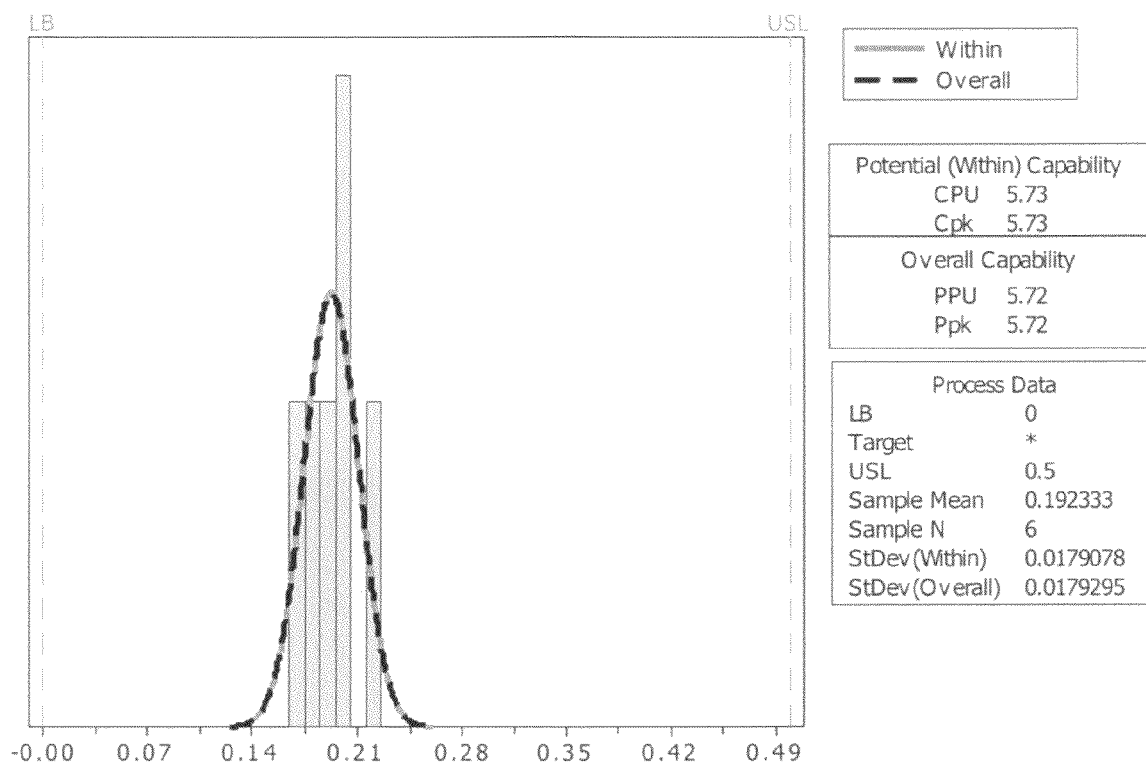
FIG. 2 illustrates that seeding of the crystallization process of step 1 further reduces the β-epimer levels. Presented on the left is a process capability analysis in which the wt %β-epimer is plotted for six pilot plant runs. The process capacity indexes (i.e., Cpk, Ppk) and other indices are presented on the right.

It has been discovered that addition of seed material to the reaction mixture as it cools further reduces the amount of impurities formed (see Example 2). The seed material typically comprises a crystalline form of the compound comprising Formula (II). In addition, the seed material also typically comprises a very low percentage by weight of the target impurity, such as below about 0.5% by weight. The amount of seed material added can and will vary, but addition of even trace amounts (such as a single crystal) may reduce the target impurity. In one exemplary iteration, the compound comprising Formula (I) is thebaine, the compound comprising Formula (II) is 6,14-endo-etheno-7α-acetyltetrahydrothebaine, and the target impurity to be minimized is the β epimer, i.e., 6,14-endo-etheno-7β-acetyltetrahydrothebaine. In this iteration, by way of non-limiting example, 0.001 kg of seed material comprising crystalline 6,14-endo-etheno-7α-acetyltetrahydrothebaine may be added per every 20 kg of thebaine charged to the reaction mixture. The seed material may be added as the reaction is cooling, such as for example, when the reaction is cooled to about 45° C. As illustrated in Example 2 and FIG. 2, use of this seeding protocol in combination with a solvent comprising water may reduce the amount of the 7-βepimer by as much as 90% by weight.

The yield of the compound comprising Formula (II) may vary. Typically, the yield of the compound may range from about 70% to about 95%. In one embodiment, the yield of the compound may range from about 70% to about 80%. In another embodiment, the yield of the compound may range from about 80% to about 90%. In a further embodiment, the yield of the compound may range from about 90% to about 95%.

In an exemplary embodiment, when the compound of Formula (I) is thebaine or oripavine and the compound comprising Formula (II) is 6,14-endo-etheno-7α-acetyltetrahydrothebaine or 6,14-endo-etheno-7α-acetyltetrahydrooripavine, then the amount of the 7-β epimer formed is less than about 1% by weight of the product (i.e., the compound comprising Formula (II)). In another embodiment, the amount of the 7-β epimer formed is less than about 0.75% by weight of the product. In yet another embodiment, the amount of the 7-β epimer formed is less than about 0.5% by weight of the product. In still another embodiment, the amount of the 7-β epimer formed is less than about 0.25% by weight of the product. In an exemplary embodiment, the amount of the 7-β epimer formed is less than about 0.2% by weight of the product. Stated another way, preferably the 7-α epimer formed is typically greater than 99% by weight of the product, more typically, is greater than about 99.5% by weight of the product, and in an exemplary embodiment, the amount of the 7-α epimer formed is greater than about 99.8% by weight of the product.

(b) Step 2: Conversion of Compound Comprising Formula (II) to Compound Comprising Formula (III)

In step 2 of the process, the double bond of the Diels Alder reaction product formed in step 1 is reduced. The substrate for preparation of the compound comprising Formula (III) corresponds to the compound comprising Formula (II) depicted in Reaction Scheme 1. An exemplary compound comprising Formula (II) comprises the following constituents: R, $R^6$, $R^7$, and $R^8$ are methyl; $R^2$, $R^3$, $R^4$, and $R^6$ are hydrogen; and X is oxygen.

Step 2 of the process commences with formation of a hydrogenation reaction mixture by combining the compound comprising Formula (II), with a catalyst in the presence of an aprotic solvent. Several aprotic solvents are suitable for use in the hydrogenation reaction. In an exemplary iteration, the solvent is a solvent having at least one acetate moiety, preferably a C2-C5 acetate, more preferably a C2-C3 acetate, and even more preferably a C3 acetate such as isopropyl acetate (see Examples 4-6). As used herein, the term "C2-C5 acetate" refers to all compounds having from two to five carbon atoms in addition to the acetate moiety. Likewise, the term "C2-C3 acetate" refers to all compounds having from two to three carbon atoms in addition to the acetate moiety.

The hydrogenation catalyst may comprise a catalyst that catalyzes hydrogen addition to the alkeno bridge, preferably the etheno bridge, of the compound comprising Formula (II) to produce the alkano, preferably ethano, bridge, of the compound comprising Formula (III). In preferred embodiments, the hydrogenation catalyst is a heterogeneous catalyst that is capable of being filtered from the reaction mixture. In certain preferred embodiments, the catalyst is a transition metal catalyst, optionally adsorbed onto a support such as alumina, barium sulfate, barium carbonate, calcium carbonate, carbon, and the like, and even more preferably the transition metal is a platinum-group metal, such as ruthenium, osmium, rhodium, iridium, palladium or platinum. In certain highly preferred embodiments, the platinum-group metal is palladium, optionally adsorbed onto a carbon support. Such catalysts are commercially available from suppliers such as Degussa and Engelhard. The hydrogenation catalyst loading is preferably in the range of about 1 to about 15 mole %, preferably in the range of about 5 to about 10 mole %, and most preferably in the range of about 6 to about 7 mole % of 5% palladium on charcoal.

The pressure of hydrogen gas during the hydrogenation reaction is preferably from about 10 psig to about 60 psig; more preferably from about 15 psig to about 50 psig, and even more preferably from about 20 psig to about 40 psig. In general, the hydrogenation reaction may be conducted at a temperature that ranges from about 55° C. to about 85° C. In a preferred embodiment, the temperature of the reaction may range from about 70° C. to about 75° C.

Typically, the hydrogenation reaction is allowed to proceed for a sufficient period of time until the reaction is complete, as defined above. In general, however, the hydrogenation reaction time is preferably from about 4 to about 9 hours, more preferably from about 3 to about 7 hours, and even more preferably from about 5 to about 6 hours. A distinct advantage of certain of the preferred embodiments of the step 2 reaction is the reduced reaction time using a solvent as described herein as the hydrogenation carrier medium, preferably as the reaction solvent. In contrast, the prior art typically indicates protic solvents for the hydrogenation reaction (e.g., alcoholic solvents, such as ethanol or isopropanol, or acidic solvents, such as acetic acid). Observed reaction time reductions using a solvent of the present invention, preferably a solvent having at least one acetate moiety, and even more preferably isopropyl acetate, compared to a protic solvent are from about 30% to about 70%, more preferably from about 40% to about 60%, and even more preferably from about 50% to about 55%.

A further distinct advantage of the solvent utilized in the hydrogenation reaction (e.g., isopropyl acetate) is that the amount of the compound comprising Formula (II) not hydrogenated is significantly reduced compared to use of a protic solvent, such as acetic acid. For example, applicants have discovered that use of acetic acid typically results in greater than 1% of the compound comprising Formula (II) not hydrogenated. In comparison, the use of isopropyl acetate results in complete or nearly complete hydrogenation of the compound comprising Formula (II). In an exemplary embodiment, the amount of the compound comprising Formula (II) not hydrogenated is less than about 0.05% by weight. In another embodiment, the amount of the compound comprising Formula (II) not hydrogenated is less than about 0.025% by weight. In an exemplary embodiment, the amount of the compound comprising Formula (II) not hydrogenated is less than about 0.01% by weight. Any of the compound comprising Formula (II) that goes forward from this step becomes Impurity D in the final product of the overall synthesis process (see section (I)(f) below).

After the hydrogenation reaction is substantially completed, the hydrogenation reaction mixture is typically concentrated to aide in the purification of the hydrogenation product. In this context, the catalyst is generally removed by filtration, and the solvent, such as isopropyl acetate, is partially removed by distillation. The amount of solvent removed can and will vary. In one embodiment, from about 50% to about 100% of the solvent is removed via distillation. In an exemplary embodiment, at least 80%, at least 85%, at least 90%, or greater than 95% of the solvent is removed via distillation.

In an exemplary iteration, after the solvent is removed from the hydrogenation reaction mixture an alkane is added. It has been found that addition of an alkane facilitates crystallization of the compound comprising Formula (III). The alkane may be linear, branched, or a cycloalkane. Suitable examples of alkanes include but are not limited to n-pentane, n-hexane, n-heptane, n-octane, isopentane, neopentane, isohexane, neohexane, isoheptane, neoheptane, cyclopentane, and cyclohexane. In an exemplary alternative of this embodiment, the alkane is heptane or cyclohexane. The amount of alkane added to the hydrogenation reaction mixture can and will vary without departing from the scope of the invention. In one embodiment, the amount of alkane added may range from about 0.5 to about 5 kg for each kg of hydrogenation product that is formed. In certain embodiments, the alkane may be added to the hydrogenation reaction mixture as it cools. In other embodiments, the alkane may be added to the hydrogenation reaction mixture while the mixture is heated, such as to a temperature from about 60° C. to about 90° C.

After the addition of the alkane, however, the hydrogenation reaction mixture is typically cooled to a temperature of less than about 20° C. during the crystallization process. In an exemplary embodiment, the temperature is reduced to less than about 10° C. during the crystallization process. It has been found that this crystallization process preferably removes substantially all of the 7-β-epimer impurities (of both the substrate and the product) and provides the crystalline form of the compound comprising Formula (III) preferably in a yield of least about 90% with a purity of about 95% to about 97%, or more preferably, a purity of about 98% to about 99%. Material of this quality is suitable for use in most applications without further purification by recrystallization.

(c) Step 3: Conversion of Compound Comprising Formula (III) to Compound Comprising Formula (IV)

Step 3 of the process comprises an addition (or Grignard) reaction. The substrate for preparation of the compound comprising Formula (IV) corresponds to the compound comprising Formula (III) depicted in Reaction Scheme 1. An exemplary compound comprising Formula (III) comprises the following substituents: R, $R^6$, $R^7$, and $R^8$ are methyl; $R^2$, $R^3$, $R^4$, and $R^5$ are hydrogen; and X is oxygen.

In step 3 of the process, the compound comprising Formula (III) is contacted with $R^9MgX^1$ (which is also known as a Grignard reagent). In general, $R^9$ is a hydrocarbyl or a substituted hydrocarbyl, and $X^1$, is a halogen. Preferably, $X^1$, may be chloride or bromide. In one embodiment, $R^9$ may be an alkyl, aryl, substituted alkyl, or substituted aryl. In a preferred embodiment, $R^9$ may be an alkyl or substituted alkyl. The alkyl or substituted alkyl may have about 12 carbons or less, or more preferably, about 6 carbons or less. Preferred $R^9$ groups include methyl, ethyl, n-propyl, n-butyl, t-butyl, n-amyl, cyclohexyl, and the like. In a preferred embodiment, $R^9$ may be tertiary butyl. In an exemplary embodiment, the Grignard reagent may be tertiary-butyl magnesium chloride. The molar ratio of the compound comprising Formula (III) to the Grignard reagent can and will vary. Typically, the molar ratio of the compound comprising Formula (III) to the Grignard reagent may range from about 1:1 to about 1:5. In some embodiments, the molar ratio of the compound comprising Formula (I) or (Ia) to the Grignard reagent may be 1:1.0, 1:1.5, 1:2.0, 1:2.5, 1:3.0, 1:3.5, 1:4.0, 1:4.5, or 1:5.0. In a preferred embodiment, the molar ratio of the compound comprising Formula (III) to the Grignard reagent may range from about 1:2.5 to about 1:3.5.

The solvent system used in step 3 comprises an aprotic solvent. A variety of aprotic solvents are suitable for use in the reaction of step 3. Non-limiting examples of suitable aprotic solvents include, diethoxymethane, diethyl ether, dimethyl sulfoxide (DMSO), 1,2-dimethoxyethane (DME), dimethoxymethane, bis(2-methoxyethyl)ether, hexamethylphosphoramide, methylene chloride, nitrobenzene, nitromethane, sulfolane, tetrahydrofuran (THF), 2-methyl tetrahydrofuran, and combinations thereof. Preferably, the aprotic solvent may be diethyl ether or tetrahydrofuran. In general, the solvent system may also comprise an organic solvent. Suitable organic solvents include, but are not limited to, benzene, t-butyl methylether, chlorobenzene, chloromethane, cyclohexane, dichloromethane, dichloroethane, diethyl ether, fluorobenzene, heptane, hexane, toluene, and combinations thereof. Preferably, the organic solvent may be toluene or heptane. In one exemplary embodiment, therefore, the solvent system may comprise tetrahydrofuran and toluene. In another exemplary embodiment, the solvent system may comprise toluene, heptane, and tetrahydrofuran. The weight ratio of the solvent system to the compound comprising Formula (III) may vary. In general, the weight ratio of the solvent system to the compound comprising Formula (III) may range from about 3:1 to about 30:1. In a preferred embodiment, the weight ratio of the solvent system to the compound comprising Formula (III) may range from about 7:1 to about 15:1. In some preferred embodiments, the weight ratio of the solvent system to the compound comprising Formula (III) may be about 7:1, 8:1, 9:1, 10:1, 11:1, 12:1, 13:1, 14:1, or 15:1.

In general, the step 3 reaction is conducted at a temperature that ranges from about 15° C. to about 100° C. In certain embodiments, the temperature of the reaction may be about 15°, 20°, 25°, 30°, 35°, 40°, 45°, 50°, 55°, 60°, 65°, 70°, 75°, 80°, 85°, 90°, 95°, or 100° C. The reaction is typically conducted under an inert atmosphere (i.e., nitrogen or argon), and preferably under ambient pressure.

Typically, the reaction is allowed to proceed for a sufficient period of time until the reaction is complete, essentially as defined above. Typically, the reaction is allowed to proceed for about one to two hours, or more preferably, about 1.5 hours.

Upon completion of the reaction, a quenching agent is added to the reaction mixture to quench the reaction product (i.e., the compound comprising Formula (IV)) and the unreacted Grignard reagent. A preferred quenching agent is aqueous ammonium chloride, although other quenching agents known to those skilled in the art may be used, including aqueous ethyl acetate, aqueous sodium chloride, or aqueous hydrochloric acid solutions. In general, the molar ratio of the compound comprising Formula (III) to the quenching agent may range from about 1:1 to about 1:12. In a preferred embodiment, the molar ratio of the compound comprising Formula (III) to the quenching agent may range from about 1:2 to about 1:7. In certain preferred embodiment, the molar ratio of the compound comprising Formula (III) to the quenching agent may be about 1:2, 1:2.5, 1:3, 1:3.5, 1:4, 1:4.5, 1:5, 1:5.5, 1:6, 1:6.5, or 1:7.

Typically, the compound comprising Formula (IV) is isolated by removing most of the solvent system to form a concentrated reaction mixture, and adding an alkane to the concentrated reaction mixture to facilitate crystallization of the product. The solvent system may be removed by distillation. Typically, at least about 50% of the solvent system may be removed. In one embodiment, at least about 80% of the solvent system may be removed. In a preferred embodiment, at least about 90% of the solvent system may be removed. The concentrated reaction mixture may be heated to a temperature that ranges from about 60° C. to about 120° C. before the addition of the alkane. In a preferred embodiment, the concentrated mixture may be heated to a temperature that ranges from about 80° C. to about 100° C., or more preferably from about 90°-98° C. before the addition of the alkane.

The alkane that is added to the concentrated reaction mixture may be linear, branched, or cyclic. In a preferred embodiment, the alkane may comprise from about 4 to about 20 carbons, or more preferably, from about 6 to about 12 carbons. In an exemplary embodiment, the alkane may be heptane or cyclohexane. In general, the weight ratio of the alkane to the compound comprising Formula (III) may range from about 3:1 to about 10:1. In a preferred embodiment, the weight ratio of the alkane to the compound comprising Formula (III) may range from about 4:1 to about 6:1. In some preferred embodiment, the weight ratio of the alkane to the compound comprising Formula (III) may be about 4.0:1. 4.5:1, 5.0:1. 5.5:1, or 6.0:1.

The concentrated reaction mixture comprising the alkane typically is allowed to cool, wherein the compound comprising Formula (IV) precipitates. In some embodiments, the concentrated reaction mixture comprising the alkane may be cooled to a temperature of less than about 20° C. In an exemplary embodiment, the concentrated reaction mixture comprising the alkane may be cooled to about 15° C. The cool temperature may be maintained for a period of time that ranges from about five minutes to more than ten hours. In a preferred embodiment, the cool temperature may be maintained from about 20 minutes to about 60 minutes.

The crystallized compound comprising Formula (IV) may be removed from the reaction mixture by filtration. Those of skill in the art are familiar with suitable filtration procedures. The yield of the compound comprising Formula (IV) may range from about 45% to about 55%.

Filtration of the reaction mixture also forms a filtrate, which comprises an amount of the compound comprising Formula (III) and an amount of the compound comprising Formula (IV). Typically, the amount of the compound comprising Formula (III) in the filtrate ranges from about 1 wt % to about 6 wt %, or more preferably about 3 wt %, and the amount of the compound comprising Formula (IV) in the filtrate may range from about 2 wt % to about 10 wt %, or more preferably about 5 wt %. The alkaloids in the filtrate may be reclaimed by recycling the filtrate. That is, the filtrate may be combined with a new reaction mixture comprising the compound comprising Formula (III) and a Grignard reagent, and the addition reaction is repeated. The recycling step may be performed one time, two times, three times, or four times. The yield of the compound comprising Formula (IV) increases with each recycling step. In general, the yield of the compound comprising Formula (IV) is greater than about 70% when two recycling steps are performed. As detailed in Example 8, when four recycling steps are performed, the yield of the compound comprising Formula (IV) typically increases by at least about 20% compared to when no recycling step is performed, based on virgin compound comprising Formula (III) introduced to each batch.

(d) Step 4: Conversion of Compound Comprising Formula (IV) to Compound Comprising Formula (V)

In step 4 of the process, the R group on the nitrogen is replaced with a nitrile group. The substrate for preparation of the compound comprising Formula (V) corresponds to the compound comprising Formula (IV) in Reaction Scheme 1. An exemplary compound comprising Formula (IV) comprises the following substituents: R, $R^6$, $R^7$, and $R^8$ are methyl; $R^2$, $R^3$, $R^4$, and $R^5$ are hydrogen; $R^9$ is tertiary butyl; and X is oxygen.

Step 4 comprises contacting the compound comprising Formula (IV) with $X^1CN$, as shown in Example 9. In preferred embodiments, $X^1$ may be chloride or bromide. In an exemplary embodiment, the compound comprising Formula (IV) may be contacted with cyanogen bromide. The molar ratio of the compound comprising Formula (IV) to $X^1CN$ may range from about 1:1 to about 1:5. In preferred embodiments, the molar ratio of the compound comprising Formula (IV) to $X^1CN$ may be about 1:1.0, 1:1.5, 1:2.0, 1:2.5, or 1:3. In an exemplary embodiment the molar ratio of the compound comprising Formula (IV) to $X^1CN$ may be about 1:1.5. The reaction is typically performed in the presence of a hydrogen halide scavenging agent. In preferred embodiments, the scavenging agent may be a metal carbonate or a metal bicarbonate. In an exemplary embodiment, the scavenging agent may be a potassium carbonate. The molar ratio of the compound comprising Formula (IV) to the scavenging agent may range from about 1:0.1 to about 1:3. In preferred embodiments, the molar ratio of the compound comprising Formula (IV) to the scavenging agent may be about 1:0.2, 1:0.3, 1:0.4, 1:0.5, 1:0.6, 1:0.7, 1:0.8, 1:0.9, or 1:1. In an exemplary embodiment, the molar ratio of the compound comprising Formula (IV) to the scavenging agent may be form about 1:0.3 to about 1:0.5.

The reaction mixture for step 4 also comprises a solvent. Typically, the solvent is an organic solvent. Non-limiting examples of suitable organic solvents include acetonitrile, benzene, butyl acetate, t-butyl methylether, t-butyl methylketone, chlorobenzene, chloroform, chloromethane, cyclohexane, dichloromethane, dichloroethane, diethyl ether, ethyl acetate, fluorobenzene, heptane, hexane, isobutylmethylketone, isopropyl acetate, methylethylketone, methyltetrahydrofuran, pentyl acetate, n-propyl acetate, tetrahydrofuran, toluene, and combinations thereof. In an exemplary embodiment, the solvent may be chloroform. In general, the weight ratio of the solvent to the compound comprising Formula (IV) may range from about 2:1 to about 20:1, preferably from about 3:1 to about 10:1, or more preferably from about 5:1 to about 6:1.

The reaction is typically conducted at reflux. Accordingly, the temperature of the reaction may range from about 50° C. to about 100° C. In an exemplary embodiment, the temperature of the reaction may be about 60-65° C. Although the pressure of the reaction may vary, it is typically conducted at ambient pressure. The reaction is allowed to proceed for a sufficient period of time until the reaction is complete, as defined above. The duration of the reaction may range from about 12 hours to about 20 hours.

Upon completion of the reaction, the reaction mixture is cooled and salts are removed by extraction with water. A majority of the solvent is removed by distillation. Typically, at least about 50% of the solvent may be removed. In one embodiment, at least about 80% of the solvent may be removed. In a preferred embodiment, at least about 90% of the solvent may be removed. The compound comprising Formula (V) is typically isolated by crystallization in the presence of an alcohol, such as methanol. Crystallization is facilitated by cooling the mixture to less than about 10° C., or more preferably to about 5-7° C. Alternatively, the compound may be crystallized using heptane. The yield of the compound comprising Formula (V) is generally greater than about 80%, preferably greater than about 85%, and more preferably greater than about 88%.

(e) Step 5: Conversion of Compound Comprising Formula (V) to Compound Comprising Formula (VI)

In step 5, the N-cyano and 3-O-substituted groups are hydrolyzed. The substrate for preparation of the compound comprising Formula (VI) corresponds to the compound comprising Formula (V) depicted in Reaction Scheme 1. An exemplary compound comprising Formula (V) comprises the following substituents: $R^6$, $R^7$, and $R^8$ are methyl; $R^2$, $R^3$, $R^4$, and $R^5$ are hydrogen; $R^9$ is tertiary butyl; and X is oxygen.

Step 5 comprises contacting the compound comprising Formula (V) with a hydrolysis agent (see Example 10). Typically, the hydrolysis agent is a compound having a pKa greater than about 12.0. Non-limiting examples of suitable compounds include group 1 and group 2 salts of hydroxides (such as, for example, KOH and $Ca(OH)_2$ and the like); and metal oxides (such as, for example, magnesium oxide, calcium oxide, and the like). In a preferred embodiment the hydrolysis agent may be a hydroxide of a group 1 or group 2 metal. In an exemplary embodiment, the hydrolysis agent may be potassium hydroxide. The molar ratio of the compound comprising Formula (V) to the hydrolysis agent can and will vary. Typically, the molar ratio of the compound comprising Formula (V) to the hydrolysis agent may range from about 1:1 to about 1:15. In a preferred embodiment, the molar ratio of the compound comprising Formula (V) to the hydrolysis agent may range from about 1:9 to about 1:15. In some preferred embodiments, the molar ratio of the compound comprising Formula (IV) to the hydrolysis agent may be about 1:9, 1:10, 1:11, 1:12, 1:13, 1:14, or 1:15.

The hydrolysis reaction mixture also includes an organic solvent. A variety of organic solvents are suitable for use in the process of the invention. Suitable organic solvents include, but are not limited to t-butyl methylether, diethylene glycol, triethylene glycol, and combinations thereof. In an exemplary embodiment, the solvent may be diethylene glycol. The weight ratio of the solvent to the compound comprising Formula (V) may vary. In general, the weight ratio of the solvent to the compound comprising Formula (V) may range from about 2:1 to about 10:1. In some embodiments, the weight ratio of the solvent to the compound comprising Formula (V) may be about 2:1, 3:1, 4:1, 5:1, 6:1, 7:1, 8:1, 9:1, or 10:1. In a preferred embodiment, the weight ratio of the solvent to the compound comprising Formula (V) may be about 5:1.

In general, the hydrolysis reaction is conducted at a temperature that ranges from about 125° C. to about 210° C. In some embodiment, the temperature of the reaction may be about 125°, 130°, 135°, 140°, 145°, 150°, 155°, 160°, 165°, 170°, 175°, 180°, 185°, 190°, 195°, 200°, 205°, or 210° C. In a preferred embodiment, the reaction may be conducted at a temperature that ranges from about 150° C. to about 200° C. In an exemplary embodiment, the temperature of the reaction may be about 185° C. The reaction is preferably performed under ambient pressure, and preferably in an inert atmosphere (e.g., nitrogen, helium, or argon).

In general, the pH of the reaction mixture will be at least about pH 12.0. In an exemplary embodiment, the pH of the reaction mixture may range from about pH 13.0 to about pH 14.0. Depending upon the hydrolysis agent, the pH of the reaction mixture also may be adjusted with an appropriate pH-modifying agent to attain the desired pH value. Those of skill in the art are familiar with suitable pH-modifying agents.

Typically, the reaction is allowed to proceed for a sufficient period of time until the reaction is complete, as defined above. More specifically, the reaction generally is allowed to proceed until the level of the compound comprising Formula (VI) no longer increases. Typically, the reaction is allowed to proceed for a period of time that ranges from about 2 hours to about 48 hours, or preferably from about 3 hours to about 12 hours. In some preferred embodiments, the duration of the reaction may be about 4.0, 4.5, 5.0, 5.5, 6.0, 6.5, 7.0, 7.5, 8.0, 9.0, 10, 11, or 12 hours. In an exemplary embodiment, the reaction is allowed to proceed from about four to about five hours.

Upon completion of the reaction, the reaction mixture is cooled. The reaction mixture may be cooled to a temperature that ranges from about 80° C. to about 100° C., or more preferably to about 90° C. Generally, the reaction mixture is diluted by the addition of water. The amount of water added to the reaction mixture may vary. Typically, the weight ratio of water to the compound comprising (V) ranges from about 10:1 to about 50:1. In a preferred embodiment, the weight ratio of water to the compound comprising (V) may range from about 15:1 to about 30:1. Dilution of the reaction mixture facilitates the precipitation of an impurity; namely, the partially hydrolyzed compound comprising Formula (VIb):

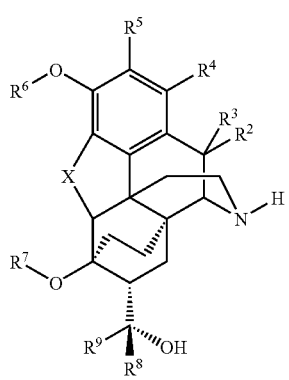

(VIb)

wherein:
R², R³, R⁴, R⁵, R⁶, R⁷, R⁸, R⁹ and X are as defined above. In an exemplary embodiment, R², R³, R⁴, and R⁵ are hydrogen; R⁶, R⁷, and R⁸ are methyl; R⁹ is tertiary butyl; and X is oxygen.

To facilitate isolation of the compound comprising Formula (VI), the pH of the reaction mixture is typically reduced to a value ranging from about 8.0 to about 9.0, wherein the compound comprising Formula (VI) crystallizes. Those of skill in the art will appreciate that a variety of pH lowering agents may be used to reduce the pH of the reaction mixture. Examples of suitable pH lowering agents include, but are not limited to, $H_2SO_4$, HCl, HBr, HI, $HNO_3$, $CF_3SO_3H$, $MeSO_3H$, $H_3PO_4$, poly $H_3PO_4$, p-methyltoluenesulfonic acid, and combinations thereof. In an exemplary embodiment, the pH of the reaction mixture may be reduced by the addition of $H_2SO_4$. The precipitated compound comprising Formula (VI) may be easily separated from the reaction mixture using procedures well known to those of skill in the art.

In an iteration of this step (and detailed in Example 11), the compound comprising Formula (VIb) may isolated and contacted with a second hydrolysis agent to form additional amounts of the compound comprising Formula (VI). Suitable hydrolysis agents are detailed above, and preferred hydrolysis agents include hydroxides of group 1 or group 1 metals. In an exemplary embodiment, the second hydrolysis agent may be potassium hydroxide. Typically, the molar ratio of the compound comprising Formula (VIb) to the second hydrolysis agent may range from about 1:1 to about 1:15. In a preferred embodiment, the molar ratio of the compound comprising Formula (VIb) to the second hydrolysis agent may range from about 1:5 to about 1:9. In some embodiments, the molar ratio of the compound comprising Formula (VIb) to the second hydrolysis agent may be about 1:5, about 1:6, about 1:7, about 1:8, or about 1:9. Suitable organic solvents, as well as reaction conditions such as temperature and pH range are detailed above. The additional compound comprising Formula (VI) may be isolated as detailed above.

The compound comprising Formula (VI) may be further purified by recrystallization. Typically, the recrystallization is conducted in a solvent system comprising a protic solvent and an aprotic solvent. Examples of suitable protic solvents include, but are not limited to, methanol, ethanol, isopropanol, n-propanol, isobutanol, n-butanol, s-butanol, t-butanol, formic acid, acetic acid, water, and combinations thereof. Examples of suitable aprotic solvents are listed above in section (I)(c). In a preferred embodiment, the solvent system comprises methanol and acetonitrile. In an exemplary embodiment, the compound comprising Formula (VI) is recrystallized in a 57% methanol in acetonitrile mixed solvent system. The mixture comprising the solvent system and the crude compound comprising Formula (VI) may be heated to facilitate dissolution of the solids. The solvent may be removed from the mixture by distillation. Preferably, at least about 40% of the solvent may be removed, more preferably about 40% to about 50% of the solvent may be removed, and even more preferably, about 50% to about 55% of the solvent may be removed. Typically, the concentrated mixture is cooled to a temperature less than about 10° C. to facilitate crystallization of the compound comprising Formula (VI).

The recrystallization step typically increases the purity of the product. In general, the weight assay of the compound comprising Formula (VI) is greater than about 90%. In one embodiment, the weight assay of the compound comprising Formula (VI) may range from about 90% to about 95%. In another embodiment, the weight assay of the compound comprising Formula (VI) may range from about 95% to about 99%. In a further embodiment, the weight assay of the compound comprising Formula (VI) may be greater than about 99%. The molar yield of the compound comprising Formula (VI) is generally at least about 65%. In general, the molar yield may range from about 65% to about 80%. In some embodiments, the molar yield may be about 65%, 66%, 67%, 68%, 69%, 70%, 71%, 72%, 73%, 74%, 75%, 76%, 77%, 78%, 79%, or 80%. In a preferred embodiment, the molar yield may range from about 65% to about 70%.

(f) Step 6: Conversion of Compound Comprising Formula (VI) to Compound Comprising Formula (VII)

Step 6 of the process comprises an alkylation reaction. The substrate for preparation of the compound comprising Formula (VII) corresponds to the compound comprising Formula (VI) depicted in Reaction Scheme 1. An exemplary compound comprising Formula (VI) comprises the following substituents: R², R³, R⁴, and R⁵ are hydrogen; R⁷ and R⁸ are methyl; R⁹ is tertiary butyl; and X is oxygen.

The step commences with formation of a reaction mixture in which the compound comprising Formula (VI) is contacted with $R^1X^1$. Preferably, R¹ is a cycloalkyl or a substituted cycloalkyl. In a preferred embodiment, R¹ may be a cycloalkyl. In an exemplary embodiment, R¹ may be cyclopropylmethyl. Preferably, X¹ may be bromide or chloride. In an especially preferred embodiment, $R^1X^1$ may be cyclopropylmethylbromide. Typically, the molar ratio of the compound comprising Formula (VI) to $R^1X^1$ will range from about 1:0.5 to about 1:1.85. For example, in some embodiments, the molar ratio may be 1:0.6, 1:0.65, 1:0.7, 1:0.75, 1:0.8, 1:0.85, 1:0.9, 1:0.95, 1:1, 1:1.05, 1:1.1, 1:1.15, 1:1.2, 1:1.25, 1:1.3, 1:1.35, 1:1.4, 1:1.45, 1:1.5, 1:1.55, 1:1.6, 1:1.65, 1:1.7, 1:1.75, 1:1.8, or 1:1.85. In an exemplary embodiment, the molar ratio may range from about 1:1 to about 1:1.35.

In general, the $R^1X^1$ compound comprises less than 0.15% by weight of an alkenyl impurity. The alkenyl impurity may be a butenyl impurity. For instance, if X¹ is bromide, the alkenyl impurity may be 4-bromo-1-butene. If X¹ is chloride, the alkenyl impurity may be 4-chloro-1-butene. In some embodiments, the $R^1X^1$ compound may comprise less than 0.14, 0.13, 0.12, 0.11, 0.10, 0.09, 0.08, 0.07, 0.06, 0.05, 0.04, 0.03, 0.02, or 0.01% by weight of the alkenyl impurity. Generally speaking, the lower the alkenyl impurity, the lower the level of Impurity A in the final product of the process (see section (I)(f) below).

If the $R^1X^1$ compound comprises greater than 0.15 percent of an alkenyl impurity, the $R^1X^1$ compound may be treated to reduce the level of the alkenyl impurity. The method selected to reduce the impurity depends, in part, on the $R^1X^1$ compound and on the alkenyl impurity. For instance, in certain embodiments, the mixture comprising the $R^1X^1$ compound may be distilled to reduce the impurity. A method for reducing the level of the alkenyl impurity is detailed in Example 16.

The reaction mixture further comprises a catalytic additive. Generally speaking, the catalytic additive is miscible in the reaction solvent and has a boiling point below 60° C. In one embodiment, the catalytic additive may be KI (i.e., potassium iodide). In another embodiment, the catalytic additive may be NaI (i.e., sodium iodide). In a further embodiment, the catalytic additive may be CsI (i.e., cesium iodide). Typically, the molar ratio of the compound comprising Formula (VI) to the catalytic additive may range from about 1:0.5 to about 1:2.5. For instance, in some embodiments, the molar ratio may be 1:0.6, 1:0.7, 1:0.8, 1:0.9, 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, or 1:2.5. In an exemplary embodiment, the molar ratio may range from about 1:1 to about 1:1.5.

The reaction mixture may also comprise $MCO_3$. In some embodiments, M is the same metal cation used in the catalytic additive. For instance, if the catalytic additive is KI, then $MCO_3$ may be $K_2CO_3$. In contrast, if the catalytic additive is NaI, then $MCO_3$ may be $NaHCO_3$ or $Na_2CO_3$. In other embodiments, $MCO_3$ may be $Cs_2CO_3$ or $CaCO_3$. Typically, the molar ratio of the compound comprising Formula (VI) to $MCO_3$ ranges from about 1:0.5 to about 1:3.5. For instance, in some embodiments, the molar ratio may be 1:0.6, 1:0.7, 1:0.8, 1:0.9, 1:1.1, 1:1.2, 1:1.3, 1:1.4, 1:1.5, 1:1.6, 1:1.7, 1:1.8, 1:1.9, 1:2.0, 1:2.1, 1:2.2, 1:2.3, 1:2.4, 1:2.5, 1:2.6, 1:2.7, 1:2.8, 1:2.9, 1:3.0, 1:3.1, 1:3.2, 1:3.3, 1:3.4, or 1:3.5. In an exemplary embodiment, the molar ratio may range from about 1:1 to about 1:2.5.

Additionally, the reaction mixture comprises a solvent. Generally speaking, the solvent will have a polarity similar to acetone. In some embodiments, the solvent may be acetone, toluene, tetrahydrofuran, acetonitrile, methyl ethyl ketone, chlorobenzene, or fluorobenzene. In an exemplary embodiment, the solvent may be acetone.

After the reaction mixture is formed, the mixture is typically heated, as described in Example 12. Generally speaking, the mixture is heated to a temperature less than about 60° C. but greater than about 50° C. For example, the mixture may be heated to a temperature of about 59° C., 58° C., 57° C., 56° C., 55° C., 54° C., 53° C., 52° C., or 51° C. Keeping the temperature below 60° C. reduces the formation of Impurity A. The reaction mixture may be heated for between about for about 4 to about 15 hours. In some embodiments, the reaction mixture may be heated for about 4, 5, 6, 7, 8, 9, 10, 11, 12, 13, 14, or 15 hours, In other embodiments, the reaction mixture may be heated for a period of time that ranges from about 5 hours to about 10 hours.

After heating, the compound comprising Formula (VII) may be precipitated by adding water, whereas the unreacted compound comprising Formula (VI) remains in solution. The precipitated product may be filtered and washed. In some instances, the precipitate may be washed with acetonitrile. In other embodiments, the precipitate may not be washed prior to recrystallization. Generally speaking, the yield of the compound comprising Formula (VII) ranges from about 65% to about 100%. In certain embodiments, the yield may be between about 84% to about 95%. In additional embodiments, the yield may be at least 84%, 85%, 86%, 87%, 88%, 89%, 90%, 91%, 92%, 93%, 94%, 95%, 96%, 97%, 98%, or 99%.

In certain embodiments, the compound comprising Formula (VII) may be recrystallized, as detailed in Example 15. The recrystallization process generally comprises dissolving the filtered product in a recrystallization solvent. Suitable recrystallization solvents may include acetonitrile alone or in combination with an alcohol, such as methanol or ethanol. In an exemplary embodiment, the recrystallization solvent may be acetonitrile. The solution may be heated to aid in the dissolution of the filtered product. For instance, in some embodiments, the solution may be heated to a temperature between about 65° C. to about 85° C. In other embodiments, the solution may be heated to about 65°, 66°, 67°, 68°, 69°, 70°, 71°, 72°, 73°, 74°, 75°, 76°, 77°, 78°, 79°, 80°, 81°, 82°, 83°, 84°, or 85° C. In still other embodiments, the solution may be heated to about 75° C. to about 80° C. In certain embodiments, the solution may be clarified. Generally speaking, if the solution is clarified, the filtration set up should be rinsed with warm solvent to recover any remaining product.

After the product is dissolved in the recrystallization solvent, the solution is distilled to remove an amount of the solvent. For example, in some embodiments, the solution is distilled to remove about 50, 55, 60, 65, 70, or 75% of the solvent. In other embodiments, the solution is distilled to remove about 60% to about 70% of the solvent. In an exemplary embodiment, about 68% of the solvent is removed. After distillation, the solution is cooled to less than about 15°, 14°, 13°, 12°, 10°, 9°, 8°, 7°, 6°, 5°, or 4° C. and stirred for about 10, 15, 20, 25, 30, 35, 40, or 45 minutes, wherein the compound comprising Formula (VII) crystallizes. The precipitate is filtered and washed with cold solvent. Typically, the recrystallization yield is greater than 50%. In some embodiments, the yield may be at least 50%, 55%, 60%, 65%, 70%, 75%, 80%, 85%, 90%, 95%, or greater than 95%. In other embodiments, the yield may be about 90% to about 94%. The recrystallized product is generally at least about 95%, 96%, 97%, 98%, 99%, or greater than 99% pure.

In general, the recrystallized compound comprising Formula (VII) comprises less than about 0.15% by weight of an individual impurity. Non-limiting examples of possible impurities include the unreacted compound comprising Formula (VI), Impurity A, i.e., 2-[17-(but-3-enyl)-4,5α-epoxy-3-hydroxy-6-methoxy-6α,14-ethano-14α-morphinan-7α-yl]-3,3-dimethylbutan-2-ol), Impurity D, i.e., 17-(cyclopropylmethyl)-α-(1,1-dimethylethyl)-4,5-epoxy-3-hydroxy-6-methoxy-α-methyl-6,14-ethenomorphinan-7-methanol, and/or Impurity E, 2-[17-(cyclopropylmethyl)-4,5α-epoxy-3,6-dihydroxy-6α,14-ethano-14α-morphinan-7α-yl]-3,3-dimethylbutan-2-ol. Impurities A, D, and E are depicted below:

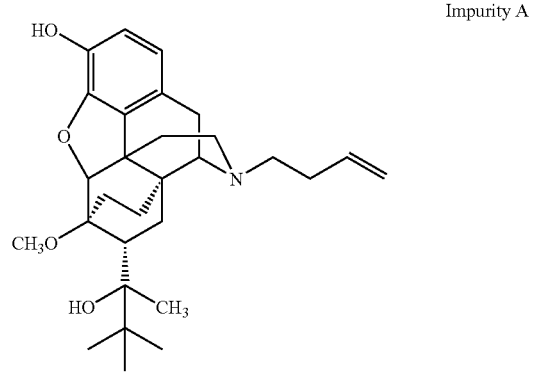

Impurity A

-continued

Impurity D

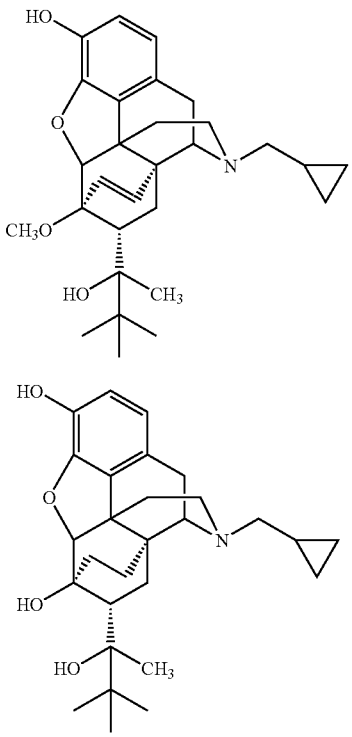

Impurity E

In one embodiment, the compound comprising Formula (VII) comprises less than 0.15% by weight of unreacted compound comprising Formula (VI), Impurity A, Impurity D, or Impurity E. In other embodiments, the compound comprising Formula (VII) comprises less than 0.14, 0.13, 0.12, 0.11, 0.10, 0.09, 0.08, 0.07, 0.06, 0.05, 0.04, 0.03, 0.02, or 0.01% by weight of unreacted compound comprising Formula (VI), Impurity A, Impurity D, or Impurity E.

The overall yield of the compound comprising Formula (VII) produced by the processes of the present invention may range from about 10% to about 30%. In some embodiments, the overall yield may range from about 12-14%, 14-16%, 16-18%, 18-20%, 20-22%, 22-24%, 24-26%, 26-28%, or 28-30%. In an exemplary embodiment, the overall yield may be range from about 17% to about 24%.

(g) Step 7: Conversion of Compound Comprising Formula (VII) to a Salt

The optional step 7 of the process comprises converting the base of the compound comprising Formula (VII) to a salt. In an exemplary embodiment, for the comprising Formula (VII), $R^2$, $R^3$, $R^4$, and $R^5$ are hydrogen; $R^7$ and $R^8$ are methyl; $R^9$ is tertiary butyl; $R^1$ is cyclopropylmethyl; and X is oxygen.

In one embodiment, the compound comprising Formula (VII) may be converted to a hydrochloride salt. For this, the compound comprising Formula (VII) is typically dissolved in isopropyl alcohol and the mixture is heated to about 50° C. An appropriate amount of concentrated hydrochloric acid may be added slowly to the mixture with stirring. The mixture may be cooled to a temperature of less than about 20° C., wherein the hydrochloride salt of the compound comprising Formula (VII) crystallizes. The precipitated compound is generally isolated by filtration, and washed with isopropyl alcohol. The isolated compound is generally dried in a vacuum oven at about 50-70° C. and 20-20 inches of Hg. The typical yield of the hydrochloride salt of the compound comprising Formula (VII) ranges from about 90-95%. In some embodiments the yield of the hydrochloride salt may be at least 90%, 91%, 92%, 93%, 94%, or 95%.

In other embodiments, another salt of the compound comprising Formula (VII) may be prepared. Exemplary salts include, without limitation, hydrobromide, phosphate, sulfate, methansulfonate, acetate, formate, tartaric acid, maleic, malic, citrate, isocitrate, succinate, lactate, gluconate, glucuronate, pyruvate, oxalate, fumarate, propionate, aspartate, glutamate, benzoate, methyl fluoride, methyl chloride, methyl bromide, methyl iodide, and the like.

The compounds comprising any of Formulas (I), (II), (III), (IV), (V), (VI), or (VII) may have either a (−) or (+) optical activity with respect to the rotation of polarized light. More specifically, each chiral center may have an R or an S configuration. The compounds formed by the processes of the invention comprise morphinans. For purposes of illustration, the ring atoms of a morphinan compound are numbered as diagrammed below.

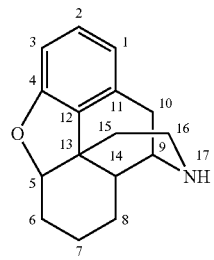

The compounds described herein may have at least six chiral centers, namely carbons C5, C6, C7, C9, C13, and C14. In general, C5 and C6 each have an R configuration, but the configuration of C7, C9, C13, and C14 may vary. The configuration of C7, C9, C13, and C14, respectively, may be RRSS, RSRR, SRSS, or SSRR, provided that the C15 and the C16 carbons are both either on the alpha face or the beta face of the molecule.

DEFINITIONS

The term "acyl," as used herein alone or as part of another group, denotes the moiety formed by removal of the hydroxy group from the group COOH of an organic carboxylic acid, e.g., RC(O), wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen which, subsequent to the reaction for which protection is employed, may be removed without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β methoxyethoxymethyl (MEM), tetrahydropyranyl (THP), ethoxy ethyl (EE), methylthiomethyl (MTM), 2 methoxy-2-propyl (MOP), 2 trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl(TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the following examples represent techniques discovered by the inventors to function well in the practice of the invention. Those of skill in the art should, however, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

Example 1

Synthesis of Compound (IIa)

Compound (Ia) (i.e., thebaine) was converted to compound (IIa) (CA index name=1-[(5α,7α)-4,5-epoxy-3,6-dimethoxy-17-methyl-6,14-ethenomorphinan-7-yl]-ethanone) via a Diels Alder reaction. For this, 575 g of wet technical grade thebaine (72 wt % by assay=414.11 g; 1.329 moles; 28% water) was suspended, under nitrogen, by agitation in 1 L of isopropanol (ACS grade), and then 264 mL of 90% methyl vinyl ketone (~2,2 equiv) and 200 mL of water were added to the mixture. The total water in the mixture was equal to the thebaine-derived water+the water added [(574× 0.28=161 mL)+200 mL=361 mL; ~35% v/v relative to isopropanol]. The mixture was then gently warmed to reflux (79°-80° C.) over a period of 4 hours using an efficient condenser with a scrubber to minimize loss of methyl vinyl ketone vapors. The reaction was slightly exothermic but not self-sustaining. The mixture was then heated at 79°-80° C. for 14 hours. (After about 1 hour at reflux, the heterogeneous slurry became homogeneous.)

The reaction mixture was cooled to room temperature over a period of about 4 hours, then cooled to 5° C. and held at this temperature for 4 hours (the red/brown solution crystallized on cooling to give a yellow-colored suspension). There was typically a 4-5° C. heat of crystallization observed in a mantle but only about 1° C. observed in a jacketed reactor. The solid was filtered and washed with 5° C. isopropanol (2×100 mL) to give compound (IIa) as a white crystalline solid. The mother liquors (which typically contained about 6% of product) were discarded as hazardous waste.

The solid product was dried under vacuum (about 22 inches Hg) for about 12 hours to give 464.99 g of white crystalline solid. Secondary drying was done in a vacuum oven at about 22 inches Hg and 60° C. for about 12 hours (with appropriate traps) if the product (464.65 g; 91.58%, m.p. 118-120° C.) was to be stored. HPLC of the solid product typically assayed at greater than 99 wt % of compound (IIa), about 0.32-0.73 wt % of the 7-β epimer, and less than 0.0087 wt % of unreacted thebaine.

Example 2

Isolation of Compound (IIe) with Seeding

Compound (IIa) was prepared essentially as detailed above in Example 1 except that seed crystals of compound (IIa) (1 g per 20 kg of thebaine) were added at 45° C. when the reaction was cooling. The assay values were similar except that the 7-β epimer levels were consistently about 0.19 wt %.

Example 3

Synthesis of Compound (IIIa) Hydrogenation in Protic Solvent

The following example illustrates the traditional hydrogenation method for reducing the double bond in compound (IIa) to form compound (IIIa) (CA index name=1-[(5α,7α)-4,5-epoxy-18,19-dihydro-3,6-dimethoxy-17-methyl-6,14-ethenomorphinan-7-yl]-ethanone). Approximately, 8.5 kg of compound (IIa) (22.3 moles) was added portion-wise with stirring to a hydrogenation reactor containing 41 L of glacial acetic acid. After the starting material was dissolved, 223 g of platinum dioxide slurried in 1 L of acetic acid was added to the resulting solution. Hydrogenation was initiated at 15 psig hydrogen pressure at room temperature. The temperature was kept below 40° C. and the reaction was run for approximately 18 hours. The catalyst was removed by filtration through diatomaceous earth, and washed with acetic acid (3×1 L). The filtrate was added slowly to a mixture of 54 L of concentrated ammonium hydroxide, 54 kg of ice, and 42 L of chloroform. The layers were separated and the aqueous phase is extracted with chloroform (2×20 L). The organic extracts were partially dried by filtration through a thick pad of diatomaceous earth. The chloroform was removed by distillation, maintaining a pot temperature of 85-90° C., and the residual oil was mixed with 32 L of hexane. The solvent was distilled off (16 L), and the mixture was cooled to 10° C. The precipitated compound (IIIa) was collected by filtration and washed with hexane (3×2 L). The crude yield was 75%. The compound (IIIa) was recrystallized from ethanol (4 mL/g) in order to remove the unreacted etheno starting material and epimeric impurities. The recovery was 93%. (If the impurity content was too high, a second recrystallization from ethanol (3 mL/g) was used.)

Example 4

Synthesis of Compound (IIIa)

Hydrogenation in Aprotic Solvent

To determine whether hydrogenation could be performed in the presence of an aprotic solvent, the following example was performed. The filtrate from a Diels-Alder reaction (in which 50 kg of thebaine was reacted with 26 kg of methyl vinyl ketone in 150 L of isopropyl acetate) was added to a hydrogenation reactor. With stirring, 5 kg of 5% palladium on charcoal, slurried in 10 L of isopropyl acetate, was added to the reactor. Hydrogen gas was introduced at a pressure of 30 psig, and the mixture was stirred and heated to 60-70° C. for 6 hours. The catalyst was removed by filtration, and the isopropyl acetate partially removed by distillation (i.e., 130-150 L of isopropyl acetate was distilled off). Heptane, 160 L, was added, and the mixture was cooled to less than 10° C. The crystallized compound (IIIa) was isolated by filtration in 90% yield, without the need for further purification (i.e., epimer levels were not detectable and alkene levels were less than about 0.2%). This example illustrates that hydrogenation in the presence of an aprotic solvent allowed for a shorter reaction time, with decreased impurities.

Example 5

Standard Hydrogenation with One Distillation Step and One Heptane Addition

The following example details a reaction conducted with a typical ratio of isopropyl acetate to compound (IIa). The hydrogenation reactor was purged with nitrogen, and 107 kg of compound (IIa) and 7.2 kg of 5% palladium on carbon (wet basis) (0.067 kg/kg of starting compound) were added to the reactor. The reactor was repurged with nitrogen and 471 kg of isopropyl acetate (4.4 kg/kg of starting compound) was added. The agitator was started and the reactor was pressurized with 30 psig hydrogen and heated to 70° C. for six hours. Upon completion of the reaction, the reactor was cooled to 30° C., the hydrogen pressure was vented, and the reactor was purged with 30 psig nitrogen. The mixture (which contained ~18 wt % of compound (IIIa) in isopropyl acetate) was reheated to about 55° C. and the catalyst was removed by filtration. The hydrogenator was then rinsed with 61 kg isopropyl acetate (0.57 kg/kg of starting compound) and the two filtrates were pooled.

Isopropyl acetate was distilled from the crude filtrate under a low nitrogen purge flow by applying steam to the tank jacket. The distillation was continued until 453 kg (~139 gallons) of isopropyl acetate was collected in the distillate receiver, and the pot temperature was between 94 and 97° C. The concentrate at the end of the distillation contained about 57 wt % solution of compound (IIIa). To this mixture, 107 kg heptane (1.0 kg/kg of starting compound) was added and the temperature was maintained between 80° and 90° C. The batch was then cooled to less than 10° C. over a four to six hour period with constant agitation (compound (IIIa) began to crystallize at a temperature between 70 and 80° C.). The slurry was stirred for at least one hour after the temperature reached 10° C., and then filtered or centrifuged to isolate compound (IIIa). The product was washed with 91 kg of heptane (0.85 kg/kg of starting compound) and dried under vacuum at 65° to 75° C. for 6 to 8 hours to give about 100 kg of compound (IIIa) (93% isolated yield).

Example 6

Dilute Hydrogenation with Two Distillation Steps and Two Heptane Additions

The following example details a hydrogenation reaction using a high charge ratio of isopropyl acetate to starting compound. This reaction was conducted essentially as that described in Example 5, except for two changes. First, a total of 1070 kg of isopropyl acetate was added to the reactor (i.e., a charge ratio of 10.0 kg isopropyl acetate per kg of starting compound). Second, the dilute reaction mixture (which contained ~9 wt % of compound (IIIa) in isopropyl acetate) only had to be heated to 35° to 40° C. in order to keep the product in solution during the catalyst filtration step.

The isopropyl acetate was distilled from the filtrate as detailed in Example 5. The first distillation was continued until 880 kg (~269 gallons) of isopropyl acetate was collected in the distillate receiver. At this point, the concentration of compound (IIIa) in the batch was about 30 wt %, and the pot temperature was between 90° and 93° C. Then, 503 kg of heptane (4.7 kg/kg of stating compound) was added, while maintaining the temperature between 65° and 90° C. A second distillation was then carried out until an additional 549 kg (~194 gal) of isopropyl acetate and heptane were distilled, and the pot temperature increased to between 95° and 98° C. After completing the second distillation, an additional 214 kg heptane (2.0 kg/kg of starting compound) was added while maintaining the temperature between 80° and 90° C. At this point, the batch composition was approximately 20 wt % of compound (IIIa), 7 wt % of isopropyl acetate, and 73 wt % of heptane. The batch was then gradually cooled to less than 10° C. over a four to six hour period, and the slurry was stirred for at least one hour after the temperature reached 10° C. The slurry was then filtered or centrifuged to isolate compound (IIIa). The solid product was washed with 91 kg heptane (0.85 kg/kg of starting material) and dried under vacuum at 65° to 75° C. for 6 to 8 hours to give about 100 kg of compound (IIIa) (93% isolated yield).

Example 7

Synthesis of Compound (IVa)

No Recycling Step

The following example details the Grignard addition reaction in which the ketone, compound (IIIa), is converted to compound (IVa) (CA index name=α-(1,1-dimethylethyl)-4, 5-epoxy-18,19-dihydro-3,6-dimethoxy-α,17-dimethyl-6, 14-ethenomorphinan-7-methanol). A ketone charge was prepared by dissolving 87.11 g of compound (IIIa) (0.2273 moles) in 266.4 g of toluene, and the ketone solution was set aside. A 2-L jacketed flask was equipped with a mechanical stirrer, a condenser, a receiver, and an addition port sealed with a septum. After purging the flask with nitrogen, a Grignard mixture was formed by adding 614.1 g of toluene and 415.2 g of a 19.22 wt % solution of tert-butylmagnesium chloride (79.81 g, 0.6828 moles) in tetrahydrofuran (THF) to the flask. The Grignard mixture was concentrated by distilling overhead 438.5 g (42.6% of the total charge) of distillate at atmospheric pressure to a final pot oil temperature of 103° C. The composition of the Grignard solution was 79.81 g of tert-BuMgCl, 142.4 g of THF, and 339.7 g of toluene. The concentrate in the flask was cooled to 60° C. The condenser and receiver were replaced with an addition funnel, and the ketone solution was added to the Grignard concentrate over a period of 31 minutes. The mixture was then stirred for an additional 90 minutes. The concentration of THF in the THF/toluene solvent mixture was 29.5 wt % before the ketone solution was added and 19.0 wt % after the ketone solution was added.

Upon completion of the reaction period, the mixture was cooled to 6° C., and 367.7 g of a 20.26 wt % solution of NH$_4$Cl (1.392 moles) in water was added over a period of 33 minutes. Then, 439.4 g of water was added, followed by 87.20 g of concentrated hydrochloric acid, which afforded a pH of 3.73. The mixture was vigorously stirred until all of the solids were dissolved. To the mixture was added 89.68 g of concentrated ammonium hydroxide, which afforded a pH of 8.77. The entire mixture was vacuum filtered through Whatman Qualitative No. 1 filter paper. The mixture was transferred to a separatory funnel and the layers were separated into a 1026.1 g lower aqueous layer and a 827.5 g upper organic layer. The aqueous layer was transferred back to the 2-L flask and 120.8 g of toluene was added. The mixture was vigorously stirred for 30 minutes. The mixture was vacuum filtered and the layers were separated into a 1001.6 g lower aqueous layer and a 119.7 g upper organic layer. The two organic layers were combined in the 2-L flask and 81.44 g of water was added. The mixture was vigorously stirred for 30 minutes. The mixture was transferred to a separatory funnel and the separated into a 177.2 g lower aqueous layer and a 920.95 g upper organic layer, which contained the alkaloids.

The 2-L flask was fitted with a short path distillation head, a condenser, and a receiver immersed in ice water. The 920.95 g organic layer was transferred to the flask. The solution was concentrated by vacuum distillation at 22 inches Hg vacuum to an overhead temperature of 75° C. and a pot oil temperature of 87° C. Approximately 760.5 g (82.5% of the charge) of distillate was collected. The distillation head was replaced with an addition funnel, which was charged with 431.4 g of heptane. The pot oil was heated to 95° C. and the heptane was added over a period of 69 minutes. The solution was cooled. Compound (IVa) crystallized at a temperature of 56° C. The mixture was cooled to 15° C. and held at that temperature for 1 hr. The mixture was vacuum filtered to yield 65.27 g of wet cake and 395.96 g of filtrate. The wet cake was dried in a vacuum oven (22 inches Hg vacuum) at 65° for 13.5 hr to yield 56.17 g of product. Further drying at 80° C. for 30 minutes afforded 55.27 g of compound (IVa). An HPLC analysis of the isolated product found 98.95 wt % of compound (IVa) and 2.72 wt % of compound (IIIa). The yield of compound (IVa) was about 55%. The filtrate contained 4.09 wt % of compound (IVa) and 2.90 wt % of compound (IIIa).

Example 8

Synthesis of Compound (IVa)

With Recycled Filtrate

A recycling process was investigated to determine whether recycling the crystallization filtrate by combining it with a new addition reaction would increase the overall isolated yield of compound (IVa). The 2-L jacketed reactor was fitted with a mechanical stirrer, a thermometer, a short path distillation setup, and a receiver. Then 395.96 g of filtrate (from Example 7) and 528.58 g of toluene were added. The solution was moderately agitated and a 22-inch Hg vacuum was applied. The solution was concentrated with distillation occurring at pot temperatures between 69° and 84° C. Approximately 847.71 g of distillate was collected, leaving 76.83 g of pot oil. HPLC analysis found that the concentrate contained 15.8 wt % of compound (IIIa) and 29.5 wt % of compound (IVa).

The concentrated filtrate was added to another addition reaction. For this, 234.27 g of toluene and 76.61 g of compound (IIIa) were added to the concentrated filtrate. The solvent exchange vessel was rinsed with toluene, which was added to the concentrate making a total of 377.71 g of compound (IIIa) solution. HPLC analysis of this solution found 23.52 wt % of compound (IIIa) and 5.77 wt % of compound (IVa). Therefore, 12% of the compound (IIIa) solution was from recycle and 88% was virgin compound (IIIa). The compound (IIIa) solution was set aside. A 2-L jacketed reactor was set up for the Grignard solvent exchange and an inert nitrogen atmosphere was established. To the 2-L flask was added 631.11 g of toluene and 444.71 g of a 19.22 wt % solution of tert-BuMgCl in THF. The solution was concentrated by atmospheric pressure distillation to a pot oil temperature of 103° C., which afforded 517.07 g of distillate. The Grignard solution in the flask was cooled to 60° and 365.0 g of the previously prepared compound (IIIa) solution was added over a period of 63 minutes. The mixture was stirred for an additional 90 minutes.

The reaction mixture was cooled to 8° C. and then quenched with 386.59 g of a 20.26 wt % solution of ammonium chloride in water. Then 473.02 g of deionized water and 113.8 g of toluene was added. The mixture was vigorously agitated and then the layers were separated into a 199.9 g lower aqueous layer and a 98.99 g upper organic layer. The two organic layers were combined in the 2-L flask and 88.35 g of deionized water was added. The mixture was aggressively stirred for 30 minutes. The layers were separated into a 88.77 g lower aqueous layer and a 852.13 g upper organic layer.

The combined organic layer was transferred to the 2-L flask and the solution was concentrated by vacuum distillation at 22 inches Hg vacuum, at pot oil temperatures of 45-88° C., and overhead temperatures up to 78° C. Approximately 662.7 g of distillate was obtained. Solids that formed were dissolved by adding 3.77 g of toluene. The solution was heated to 95° C. and 434.1 g of heptane was added over 52 minutes. The solution was cooled to 15° C. and held at that temperature for 65 minutes. Crystallization occurred at 43° C. The mixture was vacuum filtered affording 424.43 g of filtrate and 117.24 g of wet cake. The wet cake was dried in a vacuum oven at 20 inches Hg vacuum and 80° C. for 65 hr, which afforded 71.87 g of the addition product. The assay was 94.88 wt % of compound (IVa) and 4.52 wt % of compound (IIIa). Analysis of the filtrate found 5.56 wt % of the addition product and 3.03 wt % of the ketone. This procedure was repeated for all recycle batches. Table 1 presents the reaction parameters for the virgin batch and four recycle runs.

TABLE 1

Grignard Reaction Parameters.

| Run | Virgin cmpd IIIa, g (moles) | Recycled cmpd IIIa, moles | Recycled cmpd IVa, moles | t-BuMgCl, g (moles) | t-BuMgCl/ cmpd IIIa, mole ratio | THF in Toluene, wt % | Conversion to cmpd IVa, %$^a$ | Crystal Temp (° C.) |
|---|---|---|---|---|---|---|---|---|
| Virgin Batch | 87.11 (0.2273) | | | 79.81 (0.6828) | 3.00 | 12.81 | 79.30 | 56 |
| 1$^{st}$ Recycle | 76.61 (0.1999) | 0.02998 | 0.03667 | 85.47 (0.7313) | 3.18 | 12.82 | 82.88 | 43 |
| 2$^{nd}$ Recycle | 72.33 (0.1887) | 0.04966 | 0.08625 | 88.35 (0.7559) | 3.17 | 12.82 | 67.65 | 44 |
| 3$^{rd}$ Recycle | 73.11 (0.1908) | 0.03490 | 0.06574 | 89.21 (0.7623) | 3.38 | 22.86 | 70.52 | 28 |
| 4$^{th}$ Recycle | 78.1 (0.2038) | 0.0326 | 0.05595 | 92.55 (0.7919) | 3.35 | 15.26 | 76.82 | 48 |

$^a$% = 100 * (total moles compound (IVa) in reaction mixture)/((moles virgin compound (IIIa) + moles recycle compound (IIIa) + moles recycle compound (IVa)).

92.74 g of concentrated hydrochloric acid were added, which afforded a pH of 3.92. The mixture was aggressively stirred until most of the solids were dissolved. Then 100 g of concentrated ammonium hydroxide were added, to adjust the pH of the mixture to 8.79. The mixture was vacuum filtered and the filtrate was transferred to a separatory funnel. The layers were separated into a 1107.5 g lower aqueous layer and a 775.44 g upper organic layer, which contained the product. The water layer was transferred back to the 2-L flask and It was found that four recycle runs was optimal—the levels of by-products increased to unacceptable levels after the fourth recycle run. These data reveal that four recycles of the filtrates increased the yield of isolated compound (IVa) from 55% to greater than 72%, Stated another way, recycling the filtrates increased the absolute yield of compound (IVa) by 17% over virgin batches, and increased the yield 31% relative to virgin batches. Table 2 presents the yields and material balance from the recycle processes.

TABLE 2

Summary of Recycle Runs.

| Run | Virgin Cmpd IIIa, g | Isolated Product Total, g | Isolated Product Cmpd IVa, g | Isolated Product Cmpd IIIa, g | Isolated Cmpd IVa, yield %$^a$ | Assay, wt % | Material Balance, %$^b$ |
|---|---|---|---|---|---|---|---|
| Virgin Batch | 87.11 | 55.92 | 55.33 | 1.52 | 55.1 | 98.95 | 86.17 |
| 1$^{st}$ Recycle | 76.61 | 71.87 | 68.19 | 3.25 | 77.24 | 94.88 | 93.73 |

TABLE 2-continued

Summary of Recycle Runs.

|  | Virgin | Isolated Product | | | Isolated | | |
| --- | --- | --- | --- | --- | --- | --- | --- |
| Run | Cmpd IIIa, g | Total, g | Cmpd IVa, g | Cmpd IIIa, g | Cmpd IVa, yield %[a] | Assay, wt % | Material Balance, %[b] |
| $2^{nd}$ Recycle | 72.33 | 68.25 | 64.00 | 3.56 | 76.78 | 93.78 | 91.68 |
| $3^{rd}$ Recycle | 73.11 | 74.63 | 65.77 | 1.686 | 78.06 | 88.13 | 83.84 |
| $4^{th}$ Recycle | 78.10 | 77.44 | 70.60 | 2.168 | 78.44 | 91.17 | 90.84 |
| Total | 387.26 | 348.11 | 323.89 | 12.18 | 72.58 |  | 85.69 |

[a]The isolated yield is based on the amount of virgin ketone that was charged. The amounts of the alkaloids in the recycle are not included in the yield calculation. Isolated Yield, % = 100 * ((Isolated addition product, grams)/441.6)/((Virgin ketone, grams)/383.2).
[b]Material balance, % = 100 * ((323.89 + 28.17)/441.60)/((12.18 + 14.18)/383.21)/(387.26/383.21)

Example 9

Synthesis of Compound (Va)

The following examples details the reaction of compound (VIa) with cyanogen bromide to form compound (Va) (CA index name=4,5-epoxy-18,19-dihydro-7-(1-hydroxy-1,2,2-trimethylpropyl)-3,6-dimethoxy-6,14-ethenomorphinan-17-carbonitrile).

A 3-neck jacketed reaction flask was set up with a reflux condenser, thermometer, and an overhead mixer. A programmable recirculator was connected to the jacket. The reaction flask was charged with 2.48 grams of potassium carbonate, 20.05 grams of compound (IVa) (91.08 wt % assay), 75 ml of chloroform, and 8.51 grams of cyanogen bromide. The agitator was set to 120 rpm, and the reaction was run for 19 hours at reflux (i.e., pot temperature of approximately 62° C.). After the reaction was completed, the batch was cooled to 25° C. Approximately 25 ml of water was added, and the batch stirred at 300 rpm to dissolve any salts. The batch was transferred to a separatory funnel, mixed, and the layers were separated. The chloroform layer was retained. The aqueous layer was extracted twice with approximately 32 ml of chloroform each time. The aqueous layer was discarded, and the chloroform layers were combined. The total weight of the combined chloroform layers was 213.46 grams.

The chloroform layers were transferred to a still and rinsed forward with 15 ml of chloroform. The still was provided with a condenser, receiver, thermometer, an overhead mixer and a recirculator. The batch was distilled at atmospheric pressure (998.5 millibar) to a final temperature of 80.6° C. (the residue volume was 34 ml).

To the residue was added 147 ml methanol. The batch was distilled at atmospheric pressure to a final volume of 96 ml. The batch was then cooled to 6.1° C. over approximately 4 hours to crystallize compound (Va). The compound was isolated by filtering through a Buchner funnel. The product was dried under vacuum at approximately 65° C. The yield of compound (Va) was 16.29 grams with an assay of 99.09% by weight. The overall yield on a molar basis, corrected for assay, was 86.24%.

Example 10

Synthesis of Compound (VIa)

The following example details the hydrolysis of compound (Va) to form compound (VIa) (CA index name=α-(1,1-dimethylethyl)-4,5-epoxy-18,19-dihydro-3-hydroxy-6-methoxy-α-methyl-6,14-ethenomorphinan-7-methanol).

For this, potassium hydroxide pellets and diethylene glycol (DEG) were added to a Hastelloy C reactor, which was heated and agitated under a nitrogen sweep. Upon dissolution of the potassium hydroxide pellets, compound (Va) was added. The reaction mixture was heated to 185° C. for 5-8 hours. A small amount of water was removed throughout the reaction duration. When the reactor was cooled, water was added to aid in the transfer out of the vessel where the work-up begins. The now diluted reaction mixture was filtered to remove any solids (such as, e.g., the compound comprising Formula (VIc) discussed below) and the pH was adjusted to the 8-9 range. The pH adjustment initiated the precipitation of compound (VIa), and the solids were filtered off. The solids were then re-slurried in water, heated to 50-80° C. with agitation for about 1 hour. When the re-slurry was cooled to ambient temperature, compound (VIa) was filtered off and dried. Table 3 presents the results for five different hydrolysis reactions.

TABLE 3

Conversion of Compound (Va) to Compound (VIa).

| Sample # | Compound (Va) charged (g) | Crude Compound (VIa), (g) | Crude Compound (VIa), Area % | Crude Compound (VIa), Assay, % | Crude Compound (VIa), Molar Yield, % |
| --- | --- | --- | --- | --- | --- |
| 1 | 31.5 | 21.44 | 94.4 | 95 (102%) | 70.7 |
| 2 | 30 | 20.6 | 93.6 | 92.5 | 69.5 |
| 3 | 32 | 21.46 | 94.5 | 96 | 70 |
| 4 | 26 | 16.52 | 95.2 | 94 | 64.5 |
| 5 | 30 | 21.3 | 93.4 | 91.4 | 70.9 |

Due to the harsh conditions (high temperature and caustic environment) of the hydrolysis reaction that produces compound (VIa), the compound may be recrystallized, Crude compound (VIa) was purified by recrystallization using a 57% methanol in acetonitrile mixed solvent. The charge ratio was 8.9 ml of acetonitrile and 11.7 ml methanol per gram of crude compound (VIa). The crude product was transferred to a vessel equipped with heating/cooling and distillation capabilities. The mixture was heated to about 65° C. to dissolve the solids. Typically, the solution was dark brown in color and did not require filtration. Then about 50-53% of the amount of total solvent that was initially added was distilled from the mixture. The material started to crystallize at this time. When the desired amount of solvent was distilled off, the batch was cooled to less than 10° C. The crystals were isolated by filtration and then washed with 2-2.5 mL of acetonitrile per gram of crude compound (VIa) 10-15° C. The crystals were dried at 65° C. under vacuum for 12-20 hours. The recrystallization recovered about 92% (on average) with a purity >94% by assay. Table 4 shows the results of the recrystallization of compound (VIa). The alkene that ultimately forms Impurity D was partially removed from the mother liquor during this recrystallization. This recrystallization also significantly reduced the levels of compound (VIc) (see Example 11) (e.g., initially 13% by area percent was reduced to less than <1%).

TABLE 4

Recrystallization of Compound (VIa).

| Sample # | Compound (VIa) Charged (g) | Compound (VIa) Recovered (g) | Yield (%) | Assay (%) |
|---|---|---|---|---|
| 6 | 32.61 | 26.10 | 89.34 | 95.04 |
| 7 | 41.19 | 35.82 | 92.74 | 94.09 |
| 8 | 61.93 | 40.74 | 86.90 | 93.80 |
| 9 | 58.42 | 53.32 | 93.92 | 95.17 |
| 10 | 21.30 | 19.52 | 97.19 | 96.08 |
| 11 | 21.44 | 19.42 | 93.21 | 96.87 |
| Total/ Average | 236.89 | 194.92 | 92.21 | 95.18 |

Example 11

Synthesis of Compound (VIa) from 3-O-Methyl-Norbuprenorphine

During the conversion of compound (Va) to compound (VIa) a partial hydrolysis by-product (i.e., 3-O-methyl-norbuprenorphine) is formed. The by-product is compound (VIc) as depicted below:

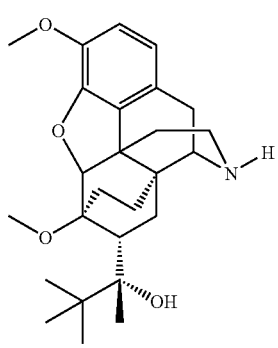

(VIc)

To determine whether compound (VIc) could be converted to compound (VIa) and, thereby, increase the overall yield of compound (VIa), the following example was devised.

First Sample. To a Hastelloy C-276 reactor, 16.2 g of potassium hydroxide (KOH) pellets and 72.5 mL of diethylene glycol (DEG) were added. The mixture was stirred and heated (to about 80°-113° C.) to dissolve the KOH. Then 14.5 g of compound (VIc) was added and the reaction mixture was heated to 185° C. for 5.25 hours. The reaction mixture was cooled to about 90° C. Approximately 500 mL of deionized water was added to the reaction mixture, and the pH of the reaction mixture (~13.8) was adjusted to pH 8.6 by the addition of about 9 mL of concentrated sulfuric acid ($H_2SO4$), and the solids were filtered off. The solids were re-slurried in water and heated to about 50-80° C. with agitation for about 1 hour. After the re-slurry cooled to room temperature, the solids were filtered off and dried to produce 11.3 g of compound (VIa). HPLC analysis revealed an assay of about 90 wt/wt % and a molar yield of about 80%.

Second Sample. KOH pellets (12.5 g) and DEG (56.15 mL) were added to a Hastelloy C-276 reactor, and the mixture was stirred and heated (to about 80°-108° C.) to dissolve the KOH. Then 11.23 g of compound (VIc) was added and the reaction mixture was heated to 185° C. for about 4.5 hours. The reaction mixture was cooled to about 90° C. and diluted with 500 mL of deionized water. The mixture was filtered to remove any solids, and the pH of the filtrate (~13.47) was adjusted to pH 8.66 by the addition of about 7.5 mL of sulfuric acid. The solids were filtered off and processed essentially as described in the first run. The product, compound (VIa) had an assay of about 92.5 wt/wt % and a molar yield of 73%.

Third Sample. KOH pellets (6.95 g) and DEG (52.9 mL) were added to a Hastelloy C-276 reactor, and the mixture was stirred and heated (to about 90°-118° C.). Then 10.58 g of compound (VIc) was added and the reaction mixture was heated to 185° C. for about 4 hours. The reaction mixture was cooled to about 90° C., diluted with 300 mL of deionized water, stirred for several minutes, and then another 300 mL of water was added. The pH of the mixture (~12.80) was adjusted to pH 8.04 by the addition of about 3 mL of concentrated sulfuric acid. The solids were filtered off and processed essentially as described in the first run. Compound (VIa) had an assay of 91.0 wt/wt % and a molar yield of 65%.

Example 12

Synthesis of Compound (VIIa)

Alkylation in Acetone

The following examples details the alkylation of compound (VIa) to produce buprenorphine or compound (VIIa) (CA index name=17-(cyclopropylmethyl)-α-(1,1-dimethylethyl)-4,5-epoxy-18,19-dihydro-3-hydroxy-6-methoxy-α-methyl-6,14-ethenomorphinan-7-methanol).

Alkylation was performed in the presence of acetone. Table 5 lists the reactants for this reaction. A mixture of 8.0 g of compound (VIa), 4.25 g of $KHCO_3$, 4.58 g (1.1 eq to bromide) of KI and 95 mL of acetone plus 0.8 mL water was charged to a 500 mL flask with a mechanical stirrer and a condenser. Then 3.39 g of cyclopropylmethyl bromide(CPM-Br) (d=1.392) was measured out into a stoppered container and washed into the reaction flask with the remaining 5 mL of acetone. The mixture was refluxed under nitrogen for 6-8 hours. If TLC indicated an incomplete reaction, it was refluxed for another 2 hours, and then cooled to room temperature.

TABLE 5

Reactants for Alkylation in Acetone.

| Reagent | MW | g | Volume | Moles | Equivalents |
|---|---|---|---|---|---|
| Compound (VIa) | 413.6 | 8.00 | | 0.0193 | 1.0 |
| KHCO₃ | 100.12 | 4.25 | | 0.0425 | 2.2 |
| CPM-Br | 135.0 | 3.39 | | 0.0251 | 1.30 |
| Acetone | | | 100 mL | | |
| KI | 166.01 | 4.58 | | 0.0276 | 1.1, to CPM-Br |
| DI water | | 0.8 | 0.8 mL | | |
| Work-up water | | | 160 mL | | |

To the stirred reaction mixture, 160 mL of water was added drop-wise over about 15-40 minutes. The mixture was heated to 55-58° C. It was stirred at that temperature for 20 minutes and then allowed to cool to 20-30° C. The mixture was filtered. The reactor and solid was washed with water (2×30 mL, about 4 mL per g of starting compound in each wash). The vacuum was turned off and 30 mL of acetonitrile was poured onto the solid and allowed to stand for a minute. Vacuum was applied to the funnel for five minutes. The sample was dried to a constant weight. The yield of compound (VIIa) was 90%, with a range of 89-91% in lab examples. With this method of isolation, the crude product typically had greater than 93 w/w % purity. It was then recrystallized to remove any remaining impurities. Crude products had these levels of purities when cyclopropylmethyl bromide(CPM-Br) with sufficient purity (i.e., low levels of 4-bromo-1-butene) was used. Table 6 presents the purity levels of different samples in which when three different grades of CPM-Br were used:

TABLE 6

Alkylation in Acetone Results.

| | | Crude Product | | |
|---|---|---|---|---|
| Sample # | Level of 4-bromo-1-butene in CPM-Br | Compound (VIIa), w/w % | Compound (VIa), w/w % | Impurity A, w/w % |
| 2 | 0.33% | 74.15 | 0.70 | 0.17 |
| 3 | 0.14% | 81.53 | 0.08 | 0.03 |
| 4 | 0.07% | 96.00 | 0.42 | 0.017 |

Additional samples were run with the lot of CPM-Br containing 0.07% 4-bromo-1-butene. The results are presented in Table 7.

TABLE 7

Additional Samples - Alkylation in Acetone.

| Sample # | Compound (VIIa) Assay | Impurity A | Crude yield |
|---|---|---|---|
| 5 | 99.46% | 0.04% | 90.5% |
| 6 | 99.65% | 0.05% | 89.0% |
| 7 | 96.82% | 0.03% | 89.5% |
| 8 | 93.51% | 0.014% | 89.8% |
| 9 | 97.08% | 0.010% | 89.7% |
| 10 | 101.13% | 0.009% | 88.5% |
| 11 | 96.09% | 0.02% | 91.0% |

Another alkylation reaction was performed using extraction. For this, a mixture of 4.04 g of compound (VIa), 2.14 g of KHCO₃, 2.24 g of KI, 1.2 mL of CPM-Br, and 60 mL of acetone was refluxed for 6.5h and then stirred overnight. To the mixture was added 80 mL of water to give a precipitate. Acetone was distilled out to a head temperature of 70° C. The pot was cooled to room temperature and 80 mL dichloromethane was added with stirring. Layers were separated. The water was extracted with 10 mL of dichloromethane. To the combined dichloromethane extracts in a clean flask was added 55 mL of acetonitrile. The mixture was distilled to a head temperature of 74° C., collecting 80 mL. At this point some solid was seen. The mixture was allowed to cool to room temperature and filtered. The flask and solid were washed with 5 mL acetonitrile. The solid was dried in vacuo to 3.19 g (70-71%). HPLC analysis indicated 99.2% compound (VIIa), 0.05% Impurity A, and 0.39% compound (VIa). The mother liquor in acetonitrile had 4% compound (VIa) and 60% compound (VIIa). This material would need to be recrystallized using the method of Example 15 to give passing material with all impurities under 0.15%.

Example 13

Synthesis of Compound (VIIa)

Alkylation in Dimethylformamide

The alkylation reaction was also performed in the presence of dimethylformamide (DMF). Table 8 presents the reagents used in this reaction. A mixture of 5.05 g of compound (VIa), 20 mL of DMF and 2.00 g NaHCO₃ was stirred and heated to 62° C. At this point the solids were mixed and partially dissolved. Cyclopropylmethyl bromide (having 0.07% of the alkenyl impurity), 1.6 mL, was added, and the mixture was taken to 85° C. and held at this temperature for 5.5 hours.

TABLE 8

Reagents for Alkylation in DMF.

| Reagent | MW | g | Volume | Moles | Equivalents |
|---|---|---|---|---|---|
| Norbuprenorphine | 413.5 | 5.05 | | 0.0122 | |
| NaHCO₃ | 84.0 | | | | |
| CPM-Br | 135.0 | 2.23 | 1.6 mL | 0.0165 | 1.35 |
| DMF | | | 20 mL | | |
| Water | | | 200 mL | | |

The reaction mixture was allowed to cool and poured slowly into a separate flask, mechanically stirred, with 75 mL water. Some of the product could be slightly gummy solid, especially on the stirrer blade. The reaction flask was rinsed two times with 1 mL of DMF, which was added to the flask. The solid obtained was filtered and washed with 50 mL of water. [In some trials, if the dried material after this wash appeared to be a good solid, it was taken directly to the hydrochloride step.] The solid batch was scooped back to the same flask and briefly boiled with 75 mL of water, then allowed to cool with stirring, to remove some residual DMF. Filtration gave a brown solid, 5.42 g (94% yield) that after drying in vacuo had 89.5% area % purity. The level of impurity A was 0.16% and the level of compound (VIa) was 0.48%. The material was not recrystallized.

The purity of the product prepared in DMF was similar to those prepared above in Example 11. A major difference, however, was that the temperature of the reaction had to be increased to 85° C. for a complete reaction to occur. Additional samples were alkylated in DMF using CPM-Br with different levels of the 4-bromo-1-butene impurity. The final product had different levels of Impurity A, as shown in Table 9.

TABLE 9

Alkylation in DMF Results.

| Sample # | Level of 4-bromo-1-butene in CPM-Br | Compound (VIIa), Area % | Compound (VIa), Area % | Impurity A, Area % |
|---|---|---|---|---|
| 12 | 0.33% | 89.08 | 2.22 | 0.19 |
| 13 | 0.33% | 82.34 | 2.05 | 0.59 |
| 14 | 0.33% | 90.40 | 0.16 | 0.34 |
| 15 | 0.14% | 99.9 | none | 0.12 |
| 16 | 0.14% | 98.13 | 0.36 | 0.12 |

Example 14

Comparison of Levels of Impurity A in Different Alkylation Reactions

Alkylations of compound (VIa) in either acetone or DMF were conducted with various lots of cyclopropylmethyl bromide (CPM-Br). The different lots had varying levels of the alkenyl impurity, 4-bromo-1-butene. This impurity alkylates in a side reaction and results in varying levels of Impurity A, as shown in the reaction scheme below:

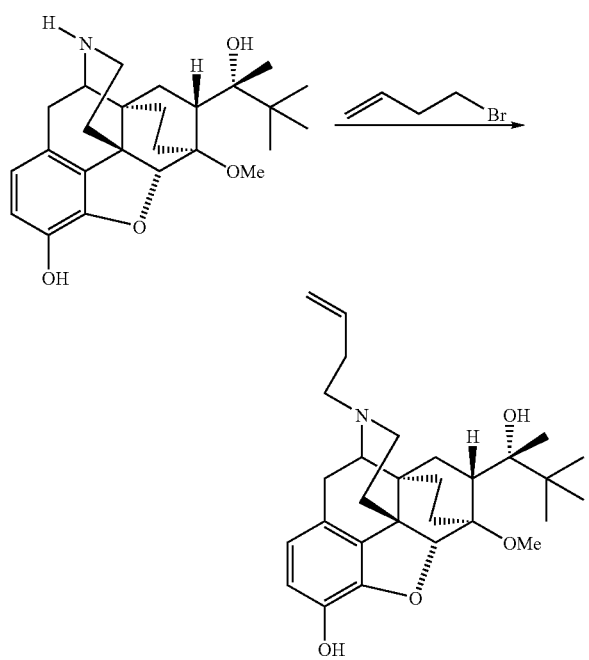

Experimental data showed that the amount of Impurity A produced is statistically related to the level of the butenyl impurity in the alkylating agent (e.g., CPM-Br). Lower levels of the butenyl impurity result in lower Impurity A levels, as the results in Table 10 show. In particular, when Lot 26 (which had a butenyl impurity level of 0.14%) was used, the acetone alkylations yielded Impurity A levels of between 0.05 and 0.06%. In contrast, using the same lot, but running the alkylation in DMF, yielded the higher Impurity A level of 0.12%.

TABLE 8

Comparison of the Levels of Impurity A.

| CPM-Bromide | Level of 4-bromo-1-butene in CPM-BR | Level of Impurity A in product |
|---|---|---|
| Alkylations in Acetone | | |
| Lot 2003 | 0.32% | 0.19 |
| | | 0.12 |
| | | 0.05 |
| | | 0.2 |
| | | 0.10 |
| Lot 26 | 0.14% | ND |
| | | 0.05 |
| | | 0.05 |
| | | 0.06 |
| Lot 117 | 0.33% | 0.16 |
| | | 0.11 |
| | | 0.10 |
| | | 0.13 |
| | | 0.15 |
| Lot 9520 | 0.69% | 0.26 |
| | | 0.21 |
| Alkylations in DMF | | |
| Lot 117 | 0.33% | 0.19 |
| | | 0.59 |
| | | 0.34 |
| Lot 26 | 0.14% | 0.12 |
| | | 0.12 |

Example 15

Recrystallization of Compound (VIIa)

The alkylation process with an acceptable alkylating agent yields a crude product of 97-99% purity containing 0.1% or less of Impurity A. This relatively clean crude product allows for recrystallization of the crude solid and therefore avoids the need for chromatographic separations. Avoiding a chromatographic separation reduces both manufacturing costs and time. Recrystallization involves the dissolution of compound (VIIa) in acetonitrile followed by distillation to optimize the recovery. The recovery after recrystallization is typically 90-92%. The recrystallization of the crude compound (VIIa) can remove 17-20% of Impurity A. If a second recrystallization is performed, the level of Impurity A can be reduced by another 6%. In addition, Impurity E may be removed by recrystallization.

The following example presents the recrystallization of several samples of crude compound (VIIa) that had an Impurity A level of 0.02%. Compound (VIIa) (45.05 g) was added to 1295 mL of acetonitrile charged to a 2-L jacketed reactor equipped with a mechanical stirrer and a condenser. The mixture was heated to 75-80° C. to dissolve the solids. [If clarification by filtration would be required, then a rinse of warm acetonitrile would also be required to recover compound (VIIa) in the filtration set up.] The solution was then set up for distillation to remove 60-70% of the solvent, with a target of 68% desired for optimal recovery. In this example, 890 mL was distilled from the batch. The batch was then cooled to <10° C. and stirred for 30 minutes. The batch was filtered and washed with 75 mL of cold acetonitrile. The sample was dried to a constant weight. The yield was 94%, with a range of 90-94% in lab examples. The weight assay of compound (VIIa) was 99.77%, with Impurity A at 0.014%. The sum of all other impurities was 0.37 by area percent.

Additional samples of compound (VIIa) were subjected to a first and a second recrystallization to determine whether the level of Impurity A could be reduced further. The results are shown in Table 11.

TABLE 11

Recrystallization Results.

| Sample # | Starting Level of Impurity A | Impurity A after 1st Recrystallization | Impurity A after 2nd Recrystallization |
|---|---|---|---|
| 18 | 0.19% | 0.16% | 0.15% |
| 19 | 0.04% | 0.03% | 0.03% |
| 20 | 0.18% | 0.10% | 0.10% |

Results of additional recrystallizations of compound (VIIa) are shown below in Tables 12A and 12B.

TABLE 12A

Recrystallization of Compound VIIa) - Part A.

| Sample # | Starting Grams (as is) | Assay (w/w %) | Grams at 100% | Grams Recovered | Assay (w/w %) | Grams at 100% | Percent Recovery |
|---|---|---|---|---|---|---|---|
| 21 | 53.92 | 98.67 | 53.20 | 46.40 | 99.28 | 46.06 | 86.58 |
| 22 | 52.52 | 98.11 | 51.53 | 44.92 | 98.39 | 44.19 | 85.77 |
| 23 | 50.96 | 96.82 | 49.34 | 43.90 | 99.11 | 43.51 | 88.19 |
| 24 | 51.03 | 93.51 | 47.72 | 44.76 | 99.36 | 44.47 | 93.20 |
| 25 | 50.98 | 95.52 | 48.70 | 44.45 | 98.26 | 43.67 | 89.69 |
| Avg | | 97.29 | | | 98.89 | | 88.68 |

TABLE 12B

Recrystallization of Compound (VIIa) - Part B.

| Sample # | Comp (VIa) (Wt. %) | Comp (VIIa) (Wt. %) | Impurity A (Wt. %) | Impurity E Area %) |
|---|---|---|---|---|
| 21 | 0.050 | 99.28 | 0.013 | 0.02 |
| 22 | 0.044 | 98.39 | 0.015 | 0.02 |
| 23 | 0.001 | 99.15 | 0.015 | 0.02 |
| 24 | 0.001 | 99.36 | 0.015 | 0.02 |
| 25 | 0.001 | 98.26 | 0.015 | 0.02 |
| Avg | 0.019 | 98.89 | 0.015 | 0.02 |

Example 16

Distillation of Cyclopropylmethyl Bromide

Cyclopropylmethyl bromide (CPM-Br) is typically synthesized at reduced temperatures to obtain selectivity of the desired product. The synthesis results in the formation of two side products, shown in the reaction scheme below:

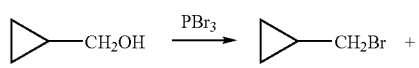

The bromocyclobutane side product is unreactive, while the 4-bromo-1-butene side product should be below 0.5% for use in the alkylations described above. If the CPM-Br is not pure enough (i.e., less than 0.5% of the butenyl impurity), the CPM-Br can be further purified. Because CPM-Br and the butenyl impurity have a narrow boiling point range, fractional distillation was used to separate the two. The distillation system utilized a >5 plate Oldershaw distillation column with a controlled splitter apparatus. The distillation was performed under reduced pressure and low temperature in a batch process. The recovery was typically 45-64%, operated at 39-40° C. and 47-52 millibar. The butenyl bromide was distilled forward and the CPM-Br with increased purity remained in the distillation vessel. Split ratios of 1.5:1 to 4:1 may be used. Results of the distillation process are shown in Table 13 below.

TABLE 13

Distillation Results.

| Run # | Initial Charge (g) | Purified (g) | Initial Impurity (%) | Final Impurity (%) | Purity (%) | Recovery (%) |
|---|---|---|---|---|---|---|
| 1 | 306.24 | 130.89 | 2.29 | 0.25 | 98.67 | 42.74 |
| 2 | 451.71 | 202.24 | 0.55 | 0.13 | 99.49 | 44.77 |
| 3 | 208.80 | 102.17 | 1.18 | 0.70 | 97.91 | 48.93 |
| 4 | 584.33 | 374.09 | 0.69 | 0.16 | 99.33 | 64.02 |
| 5 | 4176 | 1785 | 0.84 | 0.15 | 99.2 | 42.74 |
| 6 | 5568 | 2728 | 0.89 | 0.14 | 99.2 | 48.99 |
| 7 | 6264 | 3065 | 0.92 | 0.15 | 98.9 | 48.93 |

Example 17

Production of Compound (VIIa) From Compound (Ia))

Reaction Scheme 2 depicts the production of compound (VIIa) (i.e., buprenorphine) from compound (Ia) (i.e., thebaine) according to one aspect of the invention.

Reaction Scheme 2

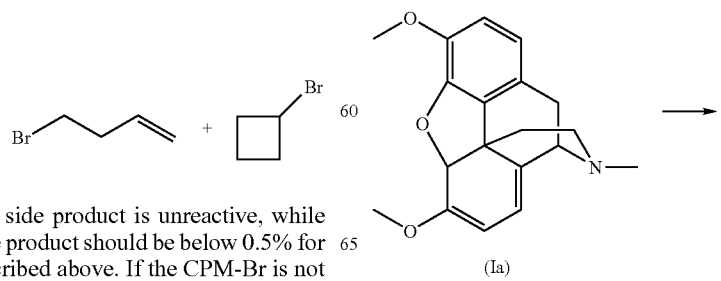

(Ia)

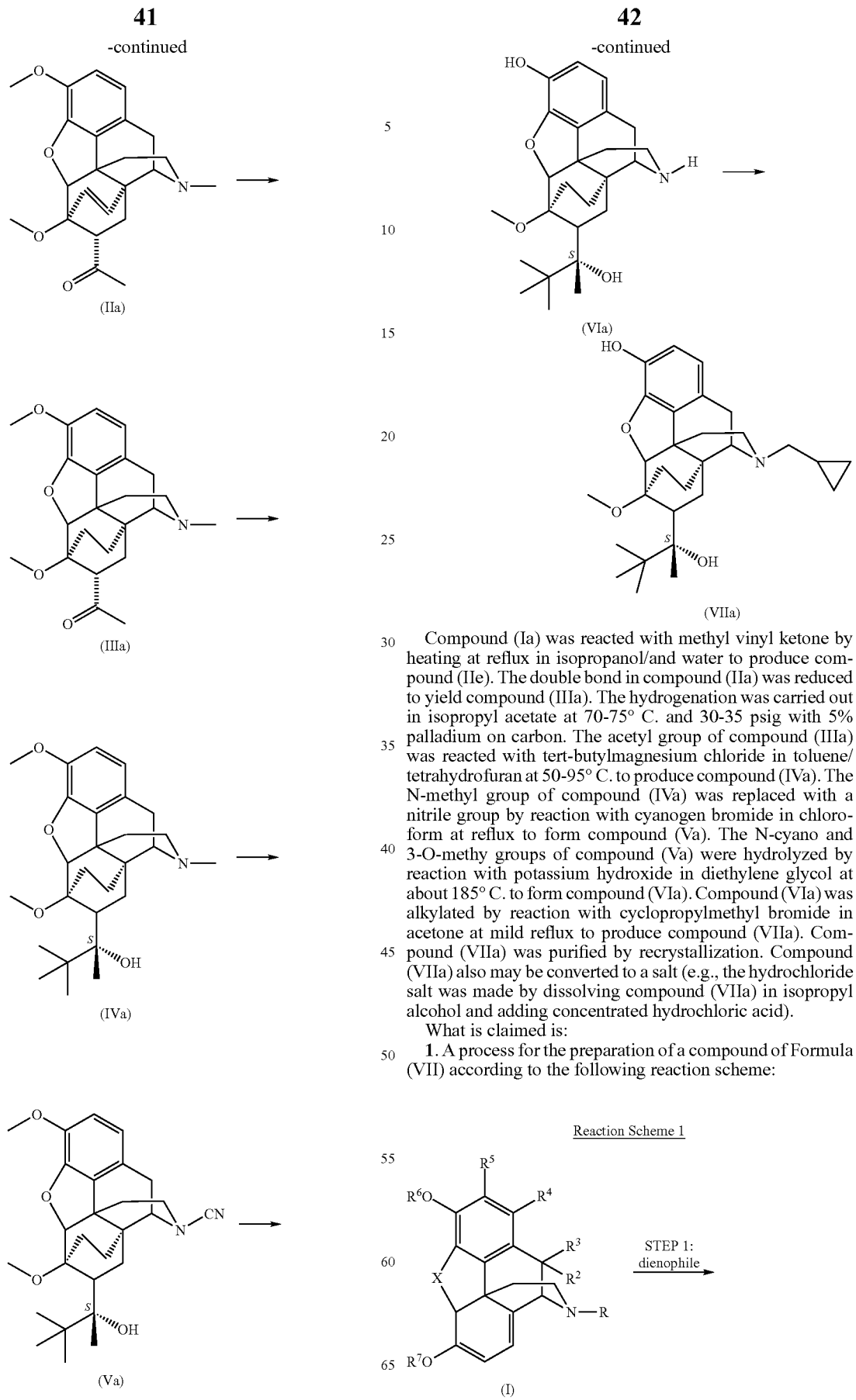

Compound (Ia) was reacted with methyl vinyl ketone by heating at reflux in isopropanol/and water to produce compound (IIe). The double bond in compound (IIa) was reduced to yield compound (IIIa). The hydrogenation was carried out in isopropyl acetate at 70-75° C. and 30-35 psig with 5% palladium on carbon. The acetyl group of compound (IIIa) was reacted with tert-butylmagnesium chloride in toluene/tetrahydrofuran at 50-95° C. to produce compound (IVa). The N-methyl group of compound (IVa) was replaced with a nitrile group by reaction with cyanogen bromide in chloroform at reflux to form compound (Va). The N-cyano and 3-O-methy groups of compound (Va) were hydrolyzed by reaction with potassium hydroxide in diethylene glycol at about 185° C. to form compound (VIa). Compound (VIa) was alkylated by reaction with cyclopropylmethyl bromide in acetone at mild reflux to produce compound (VIIa). Compound (VIIa) was purified by recrystallization. Compound (VIIa) also may be converted to a salt (e.g., the hydrochloride salt was made by dissolving compound (VIIa) in isopropyl alcohol and adding concentrated hydrochloric acid).

What is claimed is:

1. A process for the preparation of a compound of Formula (VII) according to the following reaction scheme:

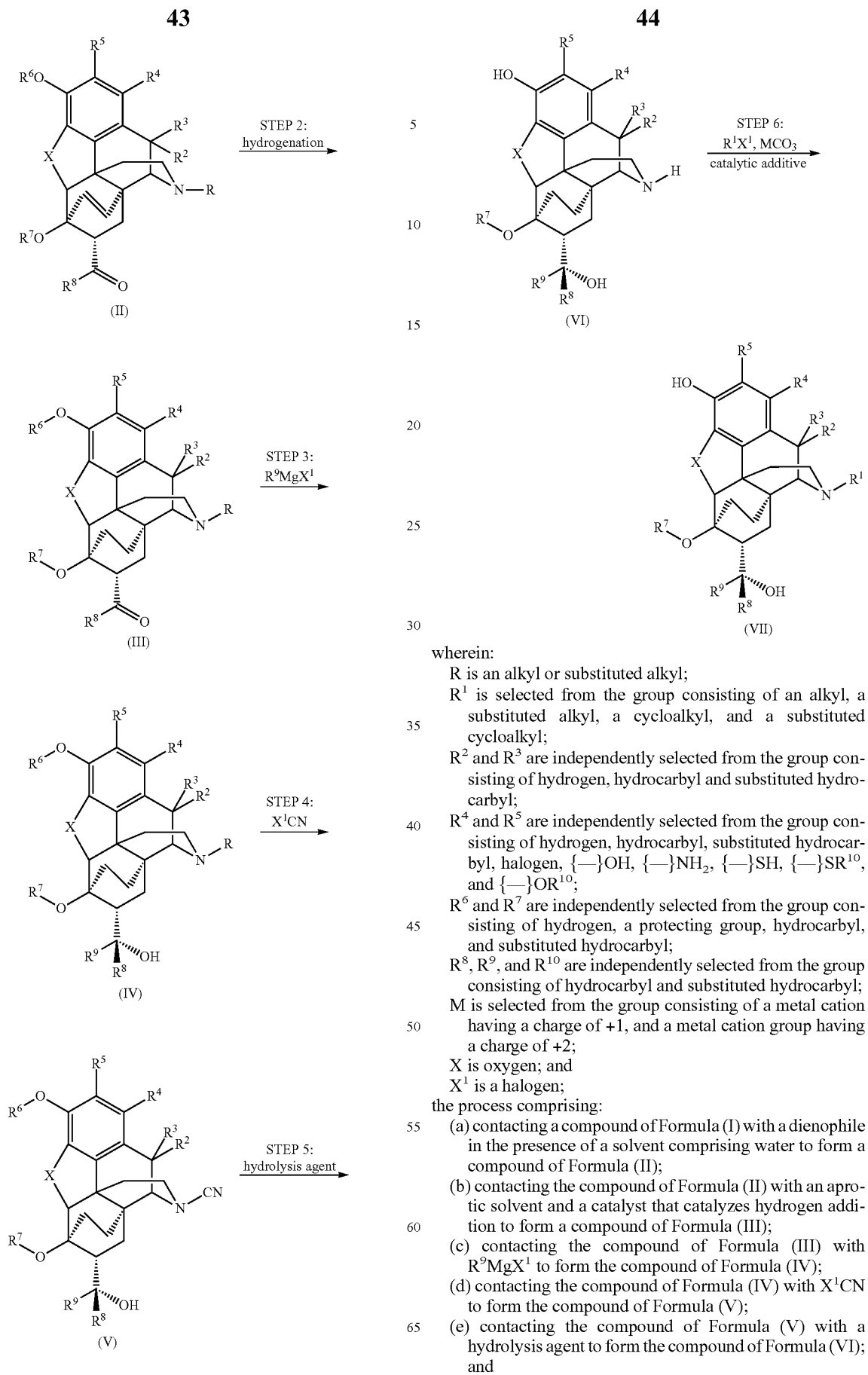

wherein:
R is an alkyl or substituted alkyl;
R$^1$ is selected from the group consisting of an alkyl, a substituted alkyl, a cycloalkyl, and a substituted cycloalkyl;
R$^2$ and R$^3$ are independently selected from the group consisting of hydrogen, hydrocarbyl and substituted hydrocarbyl;
R$^4$ and R$^5$ are independently selected from the group consisting of hydrogen, hydrocarbyl, substituted hydrocarbyl, halogen, {—}OH, {—}NH$_2$, {—}SH, {—}SR$^{10}$, and {—}OR$^{10}$;
R$^6$ and R$^7$ are independently selected from the group consisting of hydrogen, a protecting group, hydrocarbyl, and substituted hydrocarbyl;
R$^8$, R$^9$, and R$^{10}$ are independently selected from the group consisting of hydrocarbyl and substituted hydrocarbyl;
M is selected from the group consisting of a metal cation having a charge of +1, and a metal cation group having a charge of +2;
X is oxygen; and
X$^1$ is a halogen;
the process comprising:
(a) contacting a compound of Formula (I) with a dienophile in the presence of a solvent comprising water to form a compound of Formula (II);
(b) contacting the compound of Formula (II) with an aprotic solvent and a catalyst that catalyzes hydrogen addition to form a compound of Formula (III);
(c) contacting the compound of Formula (III) with R$^9$MgX$^1$ to form the compound of Formula (IV);
(d) contacting the compound of Formula (IV) with X$^1$CN to form the compound of Formula (V);
(e) contacting the compound of Formula (V) with a hydrolysis agent to form the compound of Formula (VI); and (f) contacting the compound of Formula (VI) with MCO₃ a catalytic additive, and R¹X¹, the amount of alkenyl impurity in R¹X¹ being less than 0.15% by weight, and heating the reaction mixture to a temperature of less than 60° C. to form the compound of Formula (VII).

2. The process of claim 1, wherein R, R⁶, R⁷, R⁸ and R⁹ are alkyl or substituted alkyl, and R¹ is cycloalkyl or substituted cycloalkyl.

3. The process of claim 2, wherein R², R³, R⁴, and R⁵ are hydrogen.

4. The process of claim 1, wherein R, R⁶, R⁷ and R⁸ are methyl, and R¹ is methylcyclopropyl.

5. The process of claim 1, wherein R⁹ is selected from tertiary butyl, alkyl, and substituted alkyl, provided that if R⁹ is alkyl or substituted alkyl then X¹ is chloride or bromide.

6. The process of claim 1, wherein in step (a) the solvent comprises alcohol, and from about 10% to 35% (v/v) of water; the dienophile is selected from the group consisting of methyl vinyl ketone, maleic anhydride, methyl acrylate, diethyl fumarate, benzoquinone, acetylene, 4-phenyl-1,2,4-triazolin-3,4-dione, and 2-methyl-propenal; and the reaction mixture is heated to a temperature of about 50° C. to about 100° C. for a period time that is sufficient for the conversion of a substantial portion of the compound of Formula (I) to the compound of Formula (II).

7. The process of claim 6, wherein a seed material comprising a crystalline form of the compound of Formula (II) is added to the reaction mixture as the reaction mixture is cooled to a temperature of about 5° C.; the amount of α-epimer formed at C(7) is greater than about 99.5% by weight of the amount of compound of Formula (II), and the amount of β-epimer formed at C(7) is less than about 0.50% by weight of the amount of compound of Formula (II).

8. The process of claim 1, wherein in step (b) the aprotic solvent comprises isopropyl acetate, the catalyst is a palladium catalyst adsorbed onto a carbon support, and the hydrogenation reaction is conduced at a temperature from about 65° C. to about 85° C.

9. The process of claim 8, further comprising removal of at least a portion of the isopropyl acetate after the hydrogenation reaction is substantially complete followed by the addition of an alkane as the hydrogenation reaction is cooled to less than 20° C.

10. The process of claim 1, wherein step (c) further comprises a reaction product that includes the compound of Formula (IV) and an amount of the compound of Formula (III) that is unreacted.

11. The process of claim 10, comprising:
(a) quenching the reaction product of step (c);
(b) filtering the quenched reaction product of step (a) to form a filtrate comprising an amount of the compound of Formula (III) and an amount of the compound of Formula (IV); and
(c) recycling the filtrate of step (b) by combining the filtrate with the compound of Formula (III) and R⁹MgX¹ and repeating step 1(c).

12. The process of claim 11, wherein the molar ratio of the compound of Formula (III) to R⁹MgX¹ is from about 1:1 to about 1:5; step 1(c) is conducted at a temperature of from about 15° C. to about 100° C. and in the presence of a solvent system comprising an aprotic solvent; the reaction of step 11(b) is cooled to a temperature of less than 20° C.; step 11(c) is repeated up to four times; and repeating step 11(c) four times increases the yield of the compound of Formula (IV) by at least 20% compared to when no recycling step 11(c) is performed.

13. The process of claim 1, wherein step (e) further comprises a reaction product that includes the compound of Formula (VI) and an amount of the compound of Formula (VIb); and isolating the compound of Formula (VIb) and contacting it with a second hydrolysis to form additional amounts of the compound of Formula (VI), the compound of Formula (VIb) corresponding to the following structure:

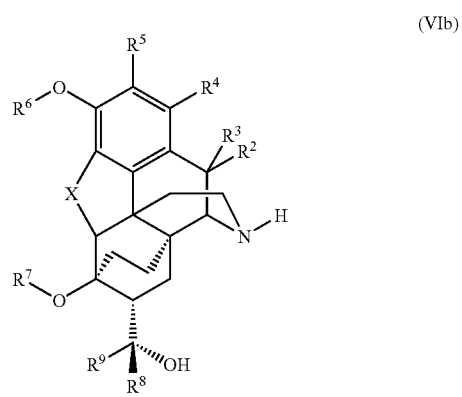

(VIb)

wherein X, R², R³, R⁴, R⁵, R⁶, R⁷, R⁸, and R⁹ are as described in claim 1.

14. The process of claim 13, wherein the first and second hydrolysis agents are each a compound having a pKa of greater than about 12.0.

15. The process of claim 14, wherein the molar ratio of the compound of Formula (VI) to the first hydrolysis agent is from about 1:9 to about 1:15; and the molar ratio of the compound of Formula (VIb) to the second hydrolysis agent is from about 1:5 to about 1:9.

16. The process of claim 15, wherein R⁶, R⁷, R⁸ and R⁹ are alkyl or substituted alkyl, and R¹ is cycloalkyl or substituted cycloalkyl.

17. The process of claim 16, wherein R², R³, R⁴, and R⁵ are hydrogen; and R⁹ is tertiary butyl.

18. The process of claim 17, further comprising contacting compound (VII) with an agent to form a salt of compound (VII).

19. The process of claim 1, wherein the optical activity of the compound of Formula (II), (III), (IV), (V), (VI), or (VII) is selected from the group consisting of (+), (−), and combinations thereof; the configuration of each of C5 and C6 is R; and the configuration of C7, C9, C13, and C14, respectively, is selected from the group consisting of may be RRSS, RSRR, SRSS, and SSRR, provided that the C15 and the C16 carbons are both either on the alpha face or the beta face of the molecule.

20. The process of claim 1, wherein compound (VII) is (−)-buprenorphine.

* * * * *